(12) United States Patent
Herron et al.

(10) Patent No.: US 10,700,284 B2
(45) Date of Patent: Jun. 30, 2020

(54) PHOTOACTIVE COMPOSITION

(71) Applicant: LG Chem, Ltd., Seoul (KR)

(72) Inventors: Norman Herron, Newark, DE (US);
Weiying Gao, Landenberg, PA (US);
Mark A Guidry, Wilmington, DE (US)

(73) Assignee: LG Chem, Ltd. (KR)

( * ) Notice: Subject to any disclaimer, the term of this patent is extended or adjusted under 35 U.S.C. 154(b) by 118 days.

(21) Appl. No.: 15/189,812

(22) Filed: Jun. 22, 2016

(65) Prior Publication Data

US 2017/0025608 A1    Jan. 26, 2017

Related U.S. Application Data

(60) Provisional application No. 62/194,583, filed on Jul. 20, 2015.

(51) Int. Cl.

| | |
|---|---|
| *H01L 51/00* | (2006.01) |
| *C09K 11/06* | (2006.01) |
| *C09K 11/02* | (2006.01) |
| *C07C 211/61* | (2006.01) |
| *C07D 307/91* | (2006.01) |
| *C07D 213/74* | (2006.01) |
| *H01L 51/50* | (2006.01) |

(52) U.S. Cl.
CPC .......... *H01L 51/006* (2013.01); *C07C 211/61* (2013.01); *C07D 213/74* (2013.01); *C07D 307/91* (2013.01); *C09K 11/025* (2013.01); *C09K 11/06* (2013.01); *H01L 51/002* (2013.01); *H01L 51/0052* (2013.01); *H01L 51/0054* (2013.01); *H01L 51/0058* (2013.01); *H01L 51/0073* (2013.01); *C07C 2603/40* (2017.05); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/5012* (2013.01)

(58) Field of Classification Search
CPC ....................................................... H01B 1/12
See application file for complete search history.

(56) References Cited

U.S. PATENT DOCUMENTS

| | | | |
|---|---|---|---|
| 2004/0102577 A1 | 5/2004 | Hsu et al. | |
| 2004/0127637 A1 | 7/2004 | Hsu et al. | |
| 2005/0205860 A1 | 9/2005 | Hsu et al. | |
| 2011/0133632 A1* | 6/2011 | Lecloux ................ | C09K 11/06 313/504 |

(Continued)

FOREIGN PATENT DOCUMENTS

| | | |
|---|---|---|
| WO | 2009/018009 A1 | 2/2009 |
| WO | 2009018009 A1 | 2/2009 |

OTHER PUBLICATIONS

Wang_PhotoconductiveMaterials_ECT_vol. 18_pp. 837-860.
Y. Wang, Photoconductive Polymers, Kirk-Othmer Encyclopedia of Chemical Technology, 4th Edition, 1996, vol. 18:837-860.

*Primary Examiner* — William D Young
(74) *Attorney, Agent, or Firm* — Lerner, David, Littenberg, Krumholz & Mentlik, LLP

(57) ABSTRACT

There is disclosed a photoactive composition; and there is also disclosed an organic electronic device comprising a first electrical contact, a second electrical contact and a photoactive layer therebetween, the photoactive layer comprising the photoactive composition.

15 Claims, 2 Drawing Sheets

(56) References Cited

U.S. PATENT DOCUMENTS

2014/0319510 A1\* 10/2014 Kageyama ............ C07C 211/61
                                                            257/40
2017/0317286 A1\* 11/2017 Ito ....................... H01L 51/0061

\* cited by examiner

PHOTOACTIVE COMPOSITION

CLAIM OF BENEFIT OF PRIOR APPLICATION

This application claims the benefit of U.S. Provisional Application No. 62/194,583, filed Jul. 20, 2015, which is incorporated in its entirety herein by reference.

BACKGROUND INFORMATION

Field of the Disclosure

This disclosure relates in general to blue luminescent compounds and their use in electronic devices.

Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules, such as anthracene, thiadiazole derivatives, and coumarin derivatives are known to show electroluminescence. Metal complexes, particularly iridium and platinum complexes are also known to show electroluminescence. In some cases these small molecule compounds are present as a dopant in a host material to improve processing and/or electronic properties.

There is a continuing need for new compositions for devices.

SUMMARY

There is provided a photoactive composition comprising (a) a dopant material having Formula AI

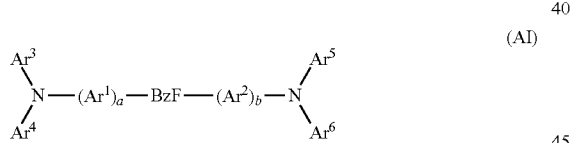

wherein:
$Ar^1$-$Ar^6$ are the same or different and are selected from the group consisting of hydrocarbon aryl, heteroaryl, and deuterated analogs thereof;
a and b are the same or different and are 0 or 1; and
BzF is selected from the group consisting of BzF-1, BzF-2, and BzF-3, having the formulae shown below

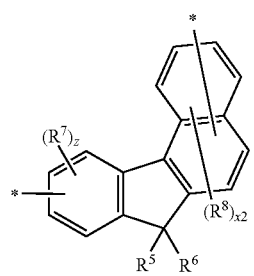

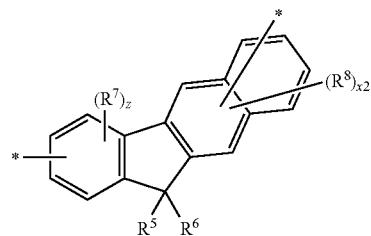

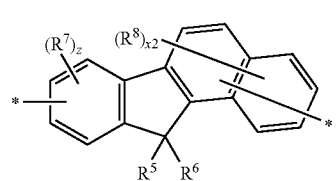

where
$R^5$ and $R^6$ are the same or different at each occurrence and are selected from the group consisting of alkyl, fluoroalkyl, hydrocarbon aryl, fluoroaryl, and deuterated analogs thereof, where two $R^5$ and $R^6$ alkyl groups can be joined together to make a cycloalkyl ring, and where two $R^5$ and $R^6$ phenyl groups can be joined to form a fluorene group;
$R^7$ and $R^8$ are the same or different at each occurrence and are selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy;
x2 is an integer from 0-5;
z is an integer from 0-3; and
* indicates a point of attachment; and
(b) a host material having Formula II

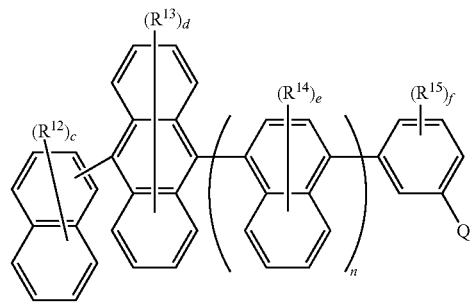

wherein:
Q is selected from the group consisting of hydrocarbon aryl, heteroaryl, and deuterated analogs thereof;
$R^{12}$-$R^{15}$ are the same or different at each occurrence and are selected from the group consisting of D, F, CN, alkyl, fluoroalkyl, hydrocarbon aryl, fluoroaryl, heteroaryl, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated silyl, deuterated germyl, deuterated alkoxy, deuterated aryloxy, deuterated fluoroalkoxy, deuterated siloxane, and deuterated siloxy;

c is an integer from 0-7;
d is an integer from 0-8;
e is an integer from 0-6;
f is an integer from 0-4; and
n is 0 or 1.

There is also provided an organic electronic device comprising a first electrical contact, a second electrical contact and a photoactive layer therebetween, the photoactive layer comprising the photoactive composition.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
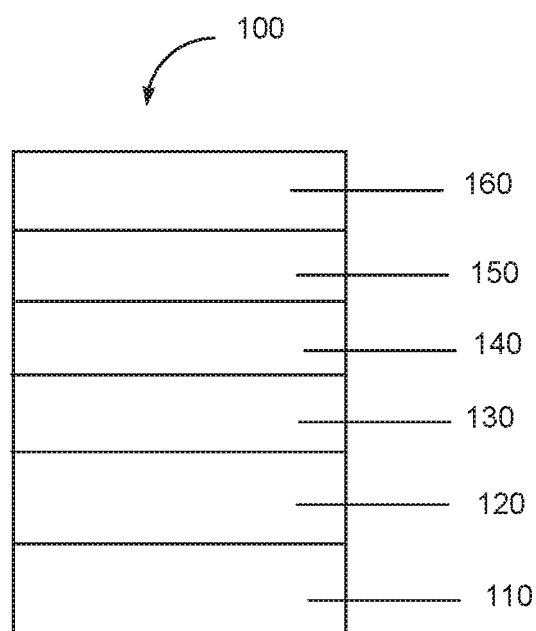
FIG. 1 includes an illustration of an organic light-emitting device including the new photoactive composition described herein.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description, and from the claims. The detailed description first addresses Definitions and Clarification of Terms followed by the Photoactive Composition, New Compounds, Devices, and finally Examples.

1. Definitions and Clarification of Terms

Before addressing details of embodiments described below, some terms are defined or clarified.

As used in the "Definitions and Clarification of Terms", R, R' and R" and any other variables are generic designations and may be the same as or different from those defined in the formulas.

The term "adjacent" as it refers to substituent groups refers to groups that are bonded to carbons that are joined together with a single or multiple bond. Exemplary adjacent R groups are shown below:

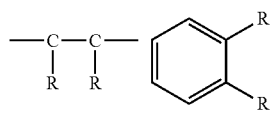

The term "alkoxy" is intended to mean the group RO—, where R is an alkyl group.

The term "alkyl" is intended to mean a group derived from an aliphatic hydrocarbon and includes a linear, a branched, or a cyclic group. A group "derived from" a compound, indicates the radical formed by removal of one or more H or D. The term "branched alkyl" is intended to mean a group derived from an aliphatic hydrocarbon that has at least one secondary or tertiary carbon. In some embodiments, an alkyl has from 1-20 carbon atoms.

The term "aromatic compound" is intended to mean an organic compound comprising at least one unsaturated cyclic group having 4n+2 delocalized pi electrons.

The term "aryl" is intended to mean a group derived from an aromatic hydrocarbon having one point of attachment. The term includes groups which have a single ring and those which have multiple rings which can be joined by a single bond or fused together. Hydrocarbon aryl groups have only carbon in the ring structures. Heteroaryl groups have at least one heteroatom in a ring structure. The term "alkylaryl" is intended to mean an aryl group having one or more alkyl substituents.

The term "aryloxy" is intended to mean the group RO—, where R is an aryl group.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "deuterated" is intended to mean that at least one hydrogen ("H") has been replaced by deuterium ("D"). The term "deuterated analog" refers to a structural analog of a compound or group in which one or more available hydrogens have been replaced with deuterium. In a deuterated compound or deuterated analog, the deuterium is present in at least 100 times the natural abundance level. The term "% deuterated" or "% deuteration" is intended to mean the ratio of deuterons to the sum of protons plus deuterons, expressed as a percentage.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The term "electron-withdrawing" as it refers to a substituent group is intended to mean a group which decreases the electron density of an aromatic ring. In some embodiments, the electron-withdrawing group ("EWG") is selected from the group consisting of fluoro, cyano, perfluoroalkyl, nitro, —$SO_2R$, where R is alkyl or perfluoroalkyl, and combinations thereof.

The term "germyl" refers to the group R₃Ge—, where R is the same or different at each occurrence and is H, D, C1-20 alkyl, deuterated alkyl, fluoroalkyl, aryl, or deuterated aryl. In some embodiments, one or more carbons in an R alkyl group are replaced with Ge.

The prefix "hetero" indicates that one or more carbon atoms have been replaced with a different atom. In some embodiments, the different atom is N, O, or S.

The term "host material" is intended to mean a material, usually in the form of a layer, to which a dopant may be added. The host material may or may not have electronic characteristic(s) or the ability to emit, receive, or filter radiation.

The terms "luminescent material", "emissive material" and "emitter" are intended to mean a material that emits light when activated by an applied voltage (such as in a light-emitting diode or light-emitting electrochemical cell). The term "blue luminescent material" is intended to mean a material capable of emitting radiation that has an emission maximum at a wavelength in a range of approximately 445-490 nm.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating or printing. Discontinuous deposition techniques include, but are not limited to, ink jet printing, gravure printing, and screen printing.

The term "organic electronic device" or sometimes just "electronic device" is intended to mean a device including one or more organic semiconductor layers or materials.

The term "photoactive" refers to a material or layer that emits light when activated by an applied voltage (such as in a light emitting diode or chemical cell) or responds to radiant energy and generates a signal with or without an applied bias voltage (such as in a photodetector or a photovoltaic cell).

The term "siloxane" refers to the group R₃SiOR₂Si—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

The term "siloxy" refers to the group R₃SiO—, where R is the same or different at each occurrence and is H, D, C1-20 alkyl, deuterated alkyl, fluoroalkyl, aryl, or deuterated aryl.

The term "silyl" refers to the group R₃Si—, where R is the same or different at each occurrence and is H, D, C1-20 alkyl, deuterated alkyl, fluoroalkyl, aryl, or deuterated aryl. In some embodiments, one or more carbons in an R alkyl group are replaced with Si.

All groups may be unsubstituted or substituted. The substituent groups are discussed below. In a structure where a substituent bond passes through one or more rings as shown below,

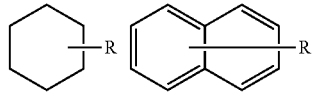

it is meant that the substituent R may be bonded at any available position on the one or more rings.

In some embodiments, the substituents are selected from the group consisting of deuterium, halide, cyano, alkyl, alkoxy, hydrocarbon aryl, heteroaryl, amino, silyl, germyl, siloxy, siloxane, deuterated alkyl, deuterated alkoxy, deuterated hydrocarbon aryl, deuterated heteroaryl, deuterated amino, deuterated silyl, deuterated germyl, deuterated siloxy, and deuterated siloxane.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics,* 81st Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic cell, and semiconductive member arts.

2. Photoactive Composition

There is provided a photoactive composition comprising:
(a) a dopant material having Formula AI

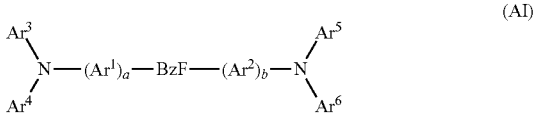

wherein:
Ar$^1$-Ar$^6$ are the same or different and are selected from the group consisting of hydrocarbon aryl, heteroaryl, and deuterated analogs thereof;
a and b are the same or different and are 0 or 1; and
BzF is selected from the group consisting of BzF-1, BzF-2, and BzF-3, having the formulae shown below

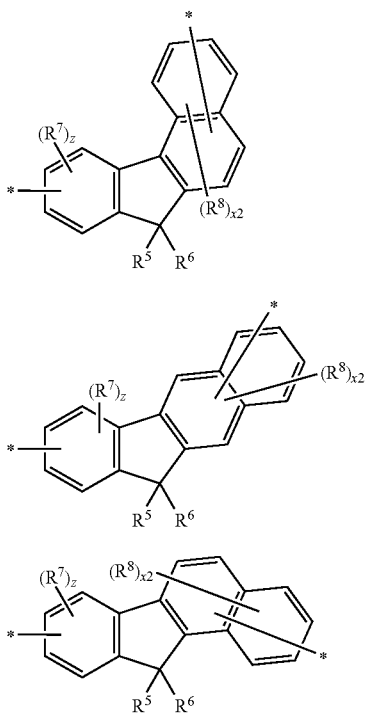

where
R$^5$ and R$^6$ are the same or different at each occurrence and are selected from the group consisting of alkyl, fluoroalkyl, hydrocarbon aryl, fluoroaryl, and deuterated analogs thereof, where two R$^5$ and R$^6$ alkyl groups can be joined together to make a cycloalkyl ring, and where two R$^5$ and R$^6$ phenyl groups can be joined to form a fluorene group;
R$^7$ and R$^8$ are the same or different at each occurrence and are selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy;
x2 is an integer from 0-5;
z is an integer from 0-3; and
* indicates a point of attachment; and
(b) a host material having Formula II

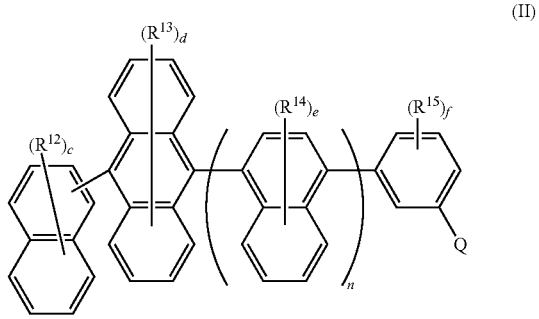

wherein:
Q is selected from the group consisting of hydrocarbon aryl, heteroaryl, and deuterated analogs thereof;
R$^{12}$-R$^{15}$ are the same or different at each occurrence and are selected from the group consisting of D, F, CN, alkyl, fluoroalkyl, hydrocarbon aryl, fluoroaryl, heteroaryl, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated silyl, deuterated germyl, deuterated alkoxy, deuterated aryloxy, deuterated fluoroalkoxy, deuterated siloxane, and deuterated siloxy;
c is an integer from 0-7;
d is an integer from 0-8;
e is an integer from 0-6;
f is an integer from 0-4; and
n is 0 or 1.

In some embodiments, the new photoactive composition has deep blue color. As used herein, the term "deep blue color" refers to a C.I.E. y-coordinate of less than 0.10, according to the C.I.E. chromaticity scale (Commission Internationale de L'Eclairage, 1931). In some embodiments, the new photoactive composition has a photoluminescence y-coordinate of less than 0.10; in some embodiments, less than 0.090.

In some embodiments, devices including the new photoactive composition have improved efficiencies. In some embodiments a device including the new photoactive composition has an efficiency greater than 4.5 cd/A at 1000 nits; in some embodiments, greater than 5.0 cd/A at 1000 nits.

In some embodiments, devices including the new photoactive composition have increased lifetime. In some embodiments, devices including the new photoactive composition have a T70 greater than 1000 hours at 50° C. As used herein, T70 refers to the time to reach 70% of initial luminance. In some embodiments, devices including the new photoactive composition have a T70 greater than 1500 hours at 50° C.

In some embodiments, electroluminescent devices including the new photoactive composition as emissive materials have deep blue color. In some embodiments, the x-coordinate is less than 0.15 and the y-coordinate is less than 0.10; in some embodiments, the y-coordinate is less than 0.090.

In some embodiments of the photoactive composition, the weight ratio of dopant to host is in the range of 99:1 to 60:1; in some embodiments, 95:5 to 70:30; in some embodiments 90:10 to 75:25.

(a) Dopant Material Having Formula AI

The dopant material in the new photoactive composition has Formula AI

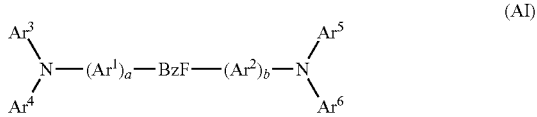

wherein:
$Ar^1$-$Ar^6$ are the same or different and are selected from the group consisting of hydrocarbon aryl, heteroaryl, and deuterated analogs thereof;
a and b are the same or different and are 0 or 1; and
BzF is selected from the group consisting of BzF-1, BzF-2, and BzF-3, having the formulae shown below

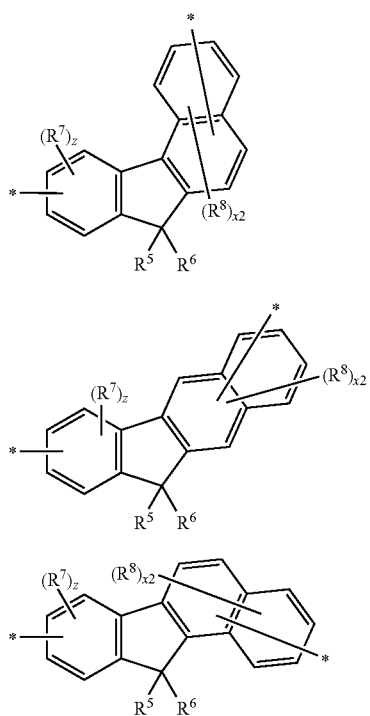

where
$R^5$ and $R^6$ are the same or different at each occurrence and are selected from the group consisting of alkyl, fluoroalkyl, hydrocarbon aryl, fluoroaryl, and deuterated analogs thereof, where two $R^5$ and $R^6$ alkyl groups can be joined together to make a cycloalkyl ring, and where two $R^5$ and $R^6$ phenyl groups can be joined to form a fluorene group;
$R^7$ and $R^8$ are the same or different at each occurrence and are selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy;
x2 is an integer from 0-5;
z is an integer from 0-3; and
* indicates a point of attachment In some embodiments of Formula AI, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula AI, deuteration is present on the core benzofluorene group.

In some embodiments of Formula AI, deuteration is present on one or more of $Ar^1$ and $Ar^2$.

In some embodiments of Formula AI, deuteration is present on one or more of the amino groups.

In some embodiments of Formula AI, deuteration is present on one or more of the above positions.

In some embodiments of Formula AI, BzF has formula BzF-1, shown above. For this core benzofluorene structure, the numbers below indicate the positions on the core.

In some embodiments of Formula AI, BzF has formula BzF-1 and at least one amino nitrogen is bonded to position 1 on the benzofluorene core.

In some embodiments of Formula AI, BzF has formula BzF-1 and at least one amino nitrogen is bonded to position 2 on the benzofluorene core.

In some embodiments of Formula AI, BzF has formula BzF-1 and at least one amino nitrogen is bonded to position 3 on the benzofluorene core.

In some embodiments of Formula AI, BzF has formula BzF-1 and at least one amino nitrogen is bonded to position 4 on the benzofluorene core.

In some embodiments of Formula AI, BzF has formula BzF-1 and at least one amino nitrogen is bonded to position 5 on the benzofluorene core.

In some embodiments of Formula AI, BzF has formula BzF-1 and at least one amino nitrogen is bonded to position 6 on the benzofluorene core.

In some embodiments of Formula AI, BzF has formula BzF-1 and at least one amino nitrogen is bonded to position 8 on the benzofluorene core.

In some embodiments of Formula AI, BzF has formula BzF-1 and at least one amino nitrogen is bonded to position 9 on the benzofluorene core.

In some embodiments of Formula AI, BzF has formula BzF-1 and at least one amino nitrogen is bonded to position 10 on the benzofluorene core.

In some embodiments of Formula AI, BzF has formula BzF-1 and at least one amino nitrogen is bonded to position 11 on the benzofluorene core.

In some embodiments of Formula AI, BzF has formula BzF-2, shown above. For this core benzofluorene structure, the numbers below indicate the positions on the core.

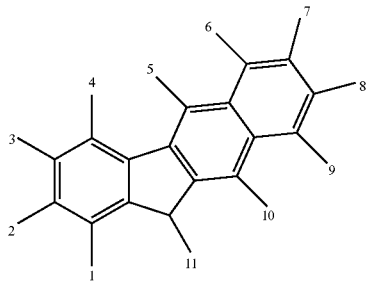

In some embodiments of Formula AI, BzF has formula BzF-2 and at least one amino nitrogen is bonded to position 1 on the benzofluorene core.

In some embodiments of Formula AI, BzF has formula BzF-2 and at least one amino nitrogen is bonded to position 2 on the benzofluorene core.

In some embodiments of Formula AI, BzF has formula BzF-2 and at least one amino nitrogen is bonded to position 3 on the benzofluorene core.

In some embodiments of Formula AI, BzF has formula BzF-2 and at least one amino nitrogen is bonded to position 4 on the benzofluorene core.

In some embodiments of Formula AI, BzF has formula BzF-2 and at least one amino nitrogen is bonded to position 5 on the benzofluorene core.

In some embodiments of Formula AI, BzF has formula BzF-2 and at least one amino nitrogen is bonded to position 6 on the benzofluorene core.

In some embodiments of Formula AI, BzF has formula BzF-2 and at least one amino nitrogen is bonded to position 7 on the benzofluorene core.

In some embodiments of Formula AI, BzF has formula BzF-2 and at least one amino nitrogen is bonded to position 8 on the benzofluorene core.

In some embodiments of Formula AI, BzF has formula BzF-2 and at least one amino nitrogen is bonded to position 9 on the benzofluorene core.

In some embodiments of Formula AI, BzF has formula BzF-2 and at least one amino nitrogen is bonded to position 10 on the benzofluorene core.

In some embodiments of Formula AI, BzF has formula BzF-3, shown above. For this core benzofluorene structure, the numbers below indicate the positions on the core.

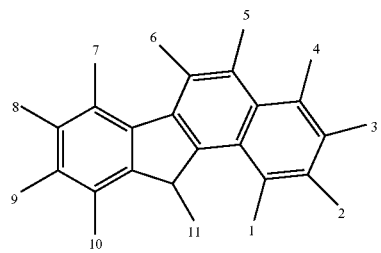

In some embodiments of Formula AI, BzF has formula BzF-3 and at least one amino nitrogen is bonded to position 1 on the benzofluorene core.

In some embodiments of Formula AI, BzF has formula BzF-3 and at least one amino nitrogen is bonded to position 2 on the benzofluorene core.

In some embodiments of Formula AI, BzF has formula BzF-3 and at least one amino nitrogen is bonded to position 3 on the benzofluorene core.

In some embodiments of Formula AI, BzF has formula BzF-3 and at least one amino nitrogen is bonded to position 4 on the benzofluorene core.

In some embodiments of Formula AI, BzF has formula BzF-3 and at least one amino nitrogen is bonded to position 5 on the benzofluorene core.

In some embodiments of Formula AI, BzF has formula BzF-3 and at least one amino nitrogen is bonded to position 6 on the benzofluorene core.

In some embodiments of Formula AI, BzF has formula BzF-3 and at least one amino nitrogen is bonded to position 7 on the benzofluorene core.

In some embodiments of Formula AI, BzF has formula BzF-3 and at least one amino nitrogen is bonded to position 8 on the benzofluorene core.

In some embodiments of Formula AI, BzF has formula BzF-3 and at least one amino nitrogen is bonded to position 9 on the benzofluorene core.

In some embodiments of Formula AI, BzF has formula BzF-3 and at least one amino nitrogen is bonded to position 10 on the benzofluorene core.

In some embodiments of formula BzF-1, formula BzF-2 or formula BzF-3, $R^5$ is selected from the group consisting of alkyl and deuterated alkyl having 1-12 carbons; in some embodiments, 3-8 carbons; in some embodiments 1-4 carbons.

In some embodiments of formula BzF-1, formula BzF-2 or formula BzF-3, $R^5$ is selected from the group consisting of aryl and deuterated aryl.

In some embodiments of formula BzF-1, formula BzF-2 or formula BzF-3, $R^5$ is selected from the group consisting of phenyl and deuterated phenyl.

In some embodiments of formula BzF-1, formula BzF-2 or formula BzF-3, $R^5$ is selected from the group consisting of fluoroalkyl and deuterated partially-fluorinated alkyl having 1-8 carbons; in some embodiments 1-4 carbons.

In some embodiments of formula BzF-1, formula BzF-2 or formula BzF-3, $R^5$ is selected from the group consisting of fluoroaryl and deuterated partially-fluorinated aryl having 6-18 ring carbons; in some embodiments 6-12 ring carbons.

All of the above described embodiments for $R^5$ apply equally to $R^6$.

In some embodiments of formula BzF-1, formula BzF-2 or formula BzF-3, $R^5$ and $R^6$ groups are joined together to form a 5- or 6-membered aliphatic ring.

In some embodiments of formula BzF-1, formula BzF-2 or formula BzF-3, $R^5$ and $R^6$ groups are joined together to form a 5- or 6-membered fluorinated aliphatic ring.

In some embodiments of formula BzF-1, formula BzF-2 or formula BzF-3, $R^5$ and $R^6$ groups are phenyl groups which are joined together to form a fluorene group.

In some embodiments of formula BzF-1, formula BzF-2 or formula BzF-3, $R^5$ and $R^6$ groups are phenyl groups which are joined together to form a fluorinated fluorene group.

In some embodiments of formula BzF-1, formula BzF-2 or formula BzF-3, z=0.

In some embodiments of formula BzF-1, formula BzF-2 or formula BzF-3, z=1.

In some embodiments of formula BzF-1, formula BzF-2 or formula BzF-3, z=2.

In some embodiments of formula BzF-1, formula BzF-2 or formula BzF-3, z=3.

In some embodiments of formula BzF-1, formula BzF-2 or formula BzF-3, z>0 and at least one $R^7$ is D.

In some embodiments of formula BzF-1, formula BzF-2 or formula BzF-3, z>0 and at least one $R^7$ is an alkyl or deuterated alkyl having 1-20 carbons; in some embodiments, 1-12 carbons; in some embodiments, 3-8 carbons.

In some embodiments of formula BzF-1, formula BzF-2 or formula BzF-3, z>0 and at least one $R^7$ is a hydrocarbon aryl group having 6-36 ring carbons. The hydrocarbon aryl group can include one or more single ring groups bonded together, one or more fused rings, or combinations thereof.

In some embodiments of formula BzF-1, formula BzF-2 or formula BzF-3, x2=0.

In some embodiments of formula BzF-1, formula BzF-2 or formula BzF-3, x2=1.

In some embodiments of formula BzF-1, formula BzF-2 or formula BzF-3, x2=2.

In some embodiments of formula BzF-1, formula BzF-2 or formula BzF-3, x2=3.

In some embodiments of formula BzF-1, formula BzF-2 or formula BzF-3, x2=4.

In some embodiments of formula BzF-1, formula BzF-2 or formula BzF-3, x2=5.

In some embodiments of formula BzF-1, formula BzF-2 or formula BzF-3, x2>0 and at least one $R^8$ is D.

In some embodiments of formula BzF-1, formula BzF-2 or formula BzF-3, x2>0 and at least one $R^8$ is an alkyl or deuterated alkyl having 1-20 carbons; in some embodiments, 1-12 carbons; in some embodiments, 3-8 carbons.

In some embodiments of formula BzF-1, formula BzF-2 or formula BzF-3, x2>0 and at least one $R^8$ is a hydrocarbon aryl group having 6-36 ring carbons. The hydrocarbon aryl group can include one or more single ring groups bonded together, one or more fused rings, or combinations thereof.

In some embodiments of Formula AI, a=0.

In some embodiments of Formula AI, a=1 and $Ar^1$ is selected from the group consisting of phenyl, naphthyl, substituted derivatives thereof, and deuterated analogs thereof. In some embodiments of the substituted derivatives, the substituent groups are selected from the group consisting of alkyl, silyl, germyl, and deuterated analogs thereof.

In some embodiments of Formula AI, b=0.

In some embodiments of Formula AI, b=1 and $Ar^2$ is selected from the group consisting of phenyl, naphthyl, substituted derivatives thereof, and deuterated analogs thereof. In some embodiments of the substituted derivatives, the substituent groups are selected from the group consisting of alkyl, silyl, germyl, and deuterated analogs thereof.

In some embodiments of Formula AI, $Ar^3$ is a hydrocarbon aryl group having 6-36 ring carbons. The hydrocarbon aryl group can include one or more single ring groups bonded together, one or more fused rings, or combinations thereof.

In some embodiments of Formula AI, $Ar^3$ has no heteroaromatic groups.

In some embodiments of Formula AI, $Ar^3$ has no amino groups.

In some embodiments of Formula AI, $Ar^3$ has Formula aa

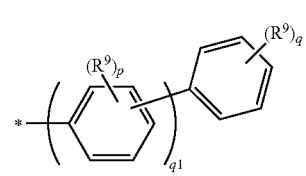

Formula aa where:
$R^9$ is the same or different at each occurrence and is selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy, where adjacent $R^9$ groups can be joined together to form an fused aromatic ring or a deuterated fused aromatic ring;
p is the same or different at each occurrence and is an integer from 0-4;
q and q1 are the same or different and are an integer from 0-5; and
* indicates the point of attachment.

In some embodiments of Formula aa, $R^9$ is selected from the group consisting of D, alkyl, hydrocarbon aryl, silyl, germyl, deuterated alkyl, deuterated hydrocarbon aryl, deuterated silyl, and deuterated germyl.

In some embodiments of Formula AI, $Ar^3$ has Formula bb

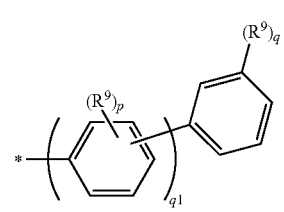

Formula bb where $R^9$, p, q, q1 and * are as in Formula aa. The above-described embodiments of $R^9$ in Formula aa apply equally to $R^9$ in Formula bb.

In some embodiments of Formula AI, $Ar^3$ is a heteroaryl or deuterated heteroaryl having at least one ring atom which is selected from the group consisting of N, O, and S.

In some embodiments of Formula AI, $Ar^3$ is an N-heteroaryl or deuterated N-heteroaryl having at least one ring atom which is N.

In some embodiments, the N-heteroaryl is derived from a compound selected from the group consisting of pyrrole, pyridine, pyrimidine, carbazole, imidazole, benzimidazole, imidazolobenzimidazole, triazole, benzotriazole, triazolopyridine, indolocarbazole, indole, indoloindole, phenanthroline, quinoline, isoquinoline, quinoxaline, substituted derivatives thereof, and deuterated analogs thereof.

In some embodiments, the N-heteroaryl is derived from a carbazole or deuterated carbazole.

In some embodiments, the N-heteroaryl is a carbazole or deuterated carbazole having formula Cz-1:

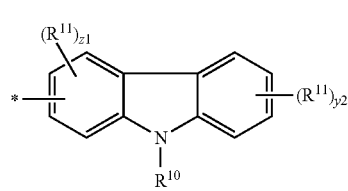

Cz-1 wherein:

$R^{10}$ is selected from the group consisting of aryl and deuterated aryl;

$R^{11}$ is the same or different at each occurrence and is selected from the group consisting of D, alkyl, silyl, aryl, deuterated alkyl, deuterated silyl, and deuterated aryl;

z1 is an integer of 0-3;

y2 is an integer of 0-4; and

* represents the point of attachment.

In some embodiments, the N-heteraryl is a carbazole or deuterated carbazole having formula Cz-2:

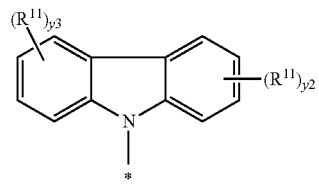

Cz-2 where y3 is an integer of 0-4 and $R^{11}$, y2, and * are as defined above for Cz-1.

In some embodiments, the N-heteroaryl is a carbazole or deuterated carbazole having formula Cz-3:

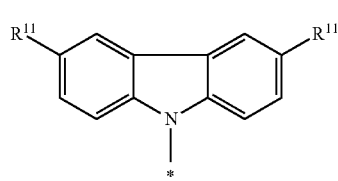

Cz-3 where $R^{11}$ and * are as defined above for Cz-1.

In some embodiments, the N-heteroaryl is a carbazole or deuterated carbazole having formula Cz-4:

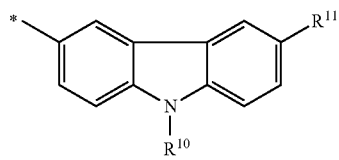

Cz-4 where $R^{10}$, $R^{11}$, and * are as defined above for Cz-1.

In some embodiments, the N-heteroaryl is a carbazole or deuterated carbazole having formula Cz-5:

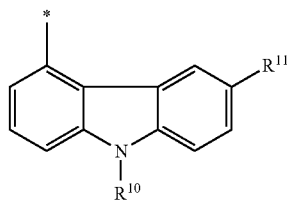

Cz-5 where $R^{10}$, $R^{11}$, and * are as defined above for Cz-1.

In some embodiments, the N-heteroaryl is derived from a compound selected from the group consisting of pyrrole, pyridine, pyrimidine, indolocarbazole, indole, indoloindole, phenanthroline, quinoline, isoquinoline, substituted derivatives thereof, and deuterated analogs thereof. In some embodiments of the substituted derivatives, the substituent is selected from the group consisting of D, alkyl, silyl, aryl, deuterated alkyl, deuterated silyl, and deuterated aryl.

In some embodiments of Formula AI, $Ar^3$ is an S-heteroaryl having at least one ring atom which is S.

In some embodiments, the S-heteroaryl is derived from a compound selected from the group consisting of thiophene, benzothiophene, dibenzothiophene, and deuterated analogs thereof.

In some embodiments, the S-heteroaryl is derived from a dibenzothiophene or deuterated dibenzothiophene.

In some embodiments, the S-heteroaryl is a dibenzothiophene or deuterated dibenzothiophene having formula DBT-1

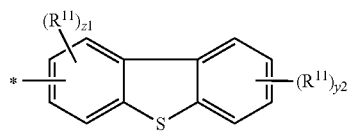

DBT-1 where $R^{11}$, y2, z1, and * are as defined above for Cz-1.

In some embodiments, the S-heteroaryl is a dibenzothiophene or deuterated dibenzothiophene having formula DBT-2

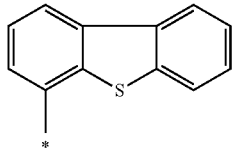

DBT-2 wherein * represents the point of attachment.

In some embodiments, the S-heteroaryl is a dibenzothiophene or deuterated dibenzothiophene having formula DBT-3:

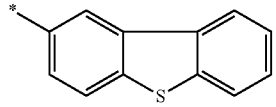

DBT-3 wherein * represents the point of attachment.

In some embodiments of Formula AI, $Ar^3$ is an O-heteroaryl having at least one ring atom that is O.

In some embodiments, the O-heteroaryl is derived from a compound selected from the group consisting of furan, benzofuran, dibenzofuran, and deuterated analogs thereof.

In some embodiments, the O-heteroaryl is derived from a dibenzofuran or deuterated dibenzofuran.

In some embodiments, the O-heteroaryl is a dibenzofuran or deuterated dibenzofuran having formula DBF-1:

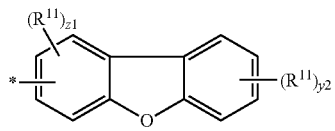

DBF-1 where $R^{11}$, y2, z1, and * are as defined above for Cz-1.

In some embodiments, the O-heteroaryl is a dibenzofuran or deuterated dibenzofuran having formula DBF-2

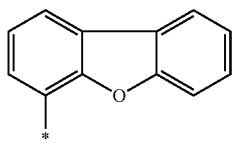

DBF-2 wherein * represents the point of attachment.

In some embodiments, the O-heteroaryl is a dibenzofuran or deuterated dibenzofuran having formula DBF-3:

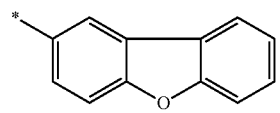

DBF-3 wherein * represents the point of attachment.

In some embodiments of Formula AI, $Ar^3$ is an N,O-heteroaryl having at least one ring atom that is N and at least one ring atom that is O.

In some embodiments, the N,O-heteroaryl is derived from a compound selected from the group consisting of oxazole, benzoxazole, and deuterated analogs thereof.

In some embodiments, the N,O-heteroaryl is a benzoxazole or deuterated benzoxazole having formula BzO-1:

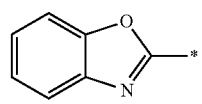

BzO-1 wherein * represents the point of attachment.

In some embodiments of Formula AI, $Ar^3$ is an N,S-heteroaryl having at least one ring atom that is N and at least one ring atom that is S.

In some embodiments, the N,S-heteroaryl is derived from a compound selected from the group consisting of thiazole, benzothiazole, and deuterated analogs thereof.

In some embodiments, the N,S-heteroaryl is a benzothiazole or deuterated benzothiazole having formula BT-1:

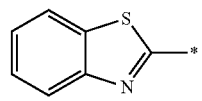

BT-1

In some embodiments of Formula AI, $Ar^3$ is selected from the group consisting of phenyl, naphthyl, Formula a, and deuterated analogs thereof.

In some embodiments of Formula AI, $Ar^3$ has substituents selected from the group consisting of D, F, CN, alkyl, alkoxy, silyl, siloxy, siloxane, germyl, hydrocarbon aryl, heteroaryl, diarylamino, carbazolyl, deuterated alkyl, deuterated alkoxy, deuterated silyl, deuterated siloxy, deuterated siloxane, deuterated gerymyl, deuterated hydrocarbon aryl, deuterated heteroaryl, deuterated diarylamino, and deuterated carbazolyl.

In some embodiments of Formula AI, $Ar^3$ has substituents selected from the group consisting of D, F, CN, alkyl, silyl, germyl, hydrocarbon aryl, deuterated alkyl, deuterated silyl, deuterated germyl, deuterated hydrocarbon aryl, and combinations thereof.

In some embodiments of Formula AI, $Ar^3$ is a hydrocarbon aryl having at least one heteroaryl substituent or a deuterated analog thereof.

All of the above-described embodiments for $Ar^3$ apply equally to $Ar^4$, $Ar^5$, and $Ar^6$.

In some embodiments of Formula AI, $Ar^3=Ar^4$.

In some embodiments of Formula AI, $Ar^3 \neq Ar^4$.

In some embodiments of Formula AI, $Ar^3=Ar^5$.
In some embodiments of Formula AI, $Ar^4=Ar^6$.
In some embodiments of Formula AI, $Ar^5=Ar^6$.
In some embodiments of Formula AI, $Ar^5 \neq Ar^6$.
In some embodiments of Formula AI, the compound has Formula AI-a

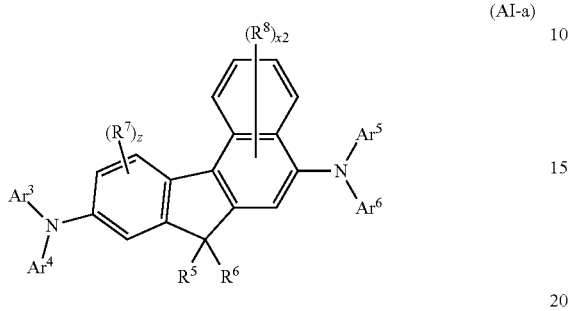

(AI-a)

where $Ar^3$-$Ar^6$, $R^5$-$R^8$, x2 and z are as defined above.

All of the above-described embodiments for $Ar^3$-$Ar^6$, $R^5$-$R^8$, x2 and z in Formula AI, apply equally to $Ar^3$-$Ar^6$, $R^5$-$R^8$, x2 and z in Formula AI-a.

Any of the above embodiments of Formula AI can be combined with one or more of the other embodiments, so long as they are not mutually exclusive. For example, the embodiment in which a=1, BzF=BzF-2 and an amino nitrogen is bonded to position 3 on the benzofluorene core can be combined with the embodiment where $Ar^1$ is phenyl. The same is true for the other non-mutually-exclusive embodiments discussed above. The skilled person would understand which embodiments were mutually exclusive and would thus readily be able to determine the combinations of embodiments that are contemplated by the present application.

In some embodiments of Formula AI, the material has Formula I

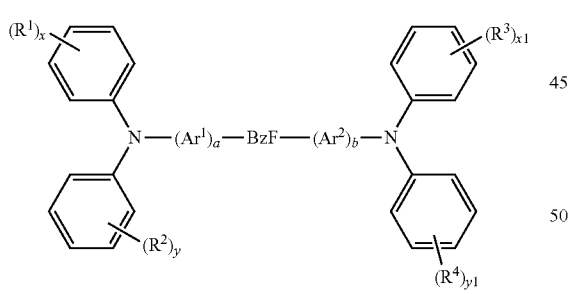

(I)

wherein:
$Ar^1$ and $Ar^2$ are the same or different and are selected from the group consisting of hydrocarbon aryl, heteroaryl, and deuterated analogs thereof;
$R^1$-$R^4$ are the same or different at each occurrence and are selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy, wherein adjacent groups selected from $R^1$-$R^4$ can be joined together to form a fused ring;
a and b are the same or different and are 0 or 1;
x, x1, y, and y1 are the same or different and are an integer from 0-5; and
BzF is selected from the group consisting of BzF-1, BzF-2, and BzF-3, having the formulae shown below

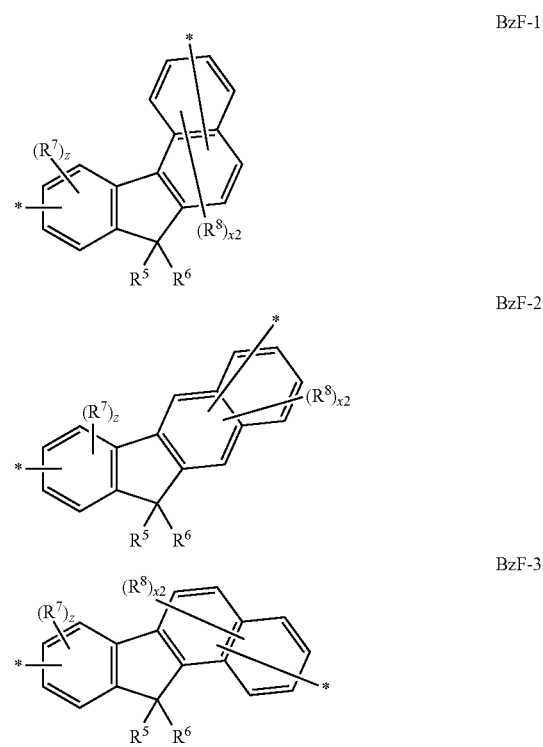

where
$R^5$ and $R^6$ are the same or different at each occurrence and are selected from the group consisting of alkyl, fluoroalkyl, hydrocarbon aryl, fluoroaryl, and deuterated analogs thereof, where two $R^5$ and $R^6$ alkyl groups can be joined together to make a cycloalkyl ring, and where two $R^5$ and $R^6$ phenyl groups can be joined to form a fluorene group;
$R^7$ and $R^8$ are the same or different at each occurrence and are selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy;
x2 is an integer from 0-5;
z is an integer from 0-3; and
* indicates a point of attachment.

In some embodiments of Formula I, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula I, deuteration is present on the core benzofluorene group.

In some embodiments of Formula I, deuteration is present on one or more of $Ar^1$ and $Ar^2$.

In some embodiments of Formula I, deuteration is present on one or more of the amino groups.

In some embodiments of Formula I, deuteration is present on one or more of the above positions.

The compounds of Formula I can be made using any technique that will yield a C—C or C—N bond. A variety of such techniques are known, such as Suzuki, Yamamoto, Stille, and metal-catalyzed C—N couplings as well as metal catalyzed and oxidative direct arylation.

Deuterated compounds can be prepared in a similar manner using deuterated precursor materials or, more generally, by treating the non-deuterated compound with deuterated solvent, such as benzene-d6, in the presence of a Lewis acid H/D exchange catalyst, such as trifluoromethanesulfonic acid, aluminum trichloride or ethyl aluminum dichloride.

All of the above-described embodiments for BzF and amino nitrogen bonding positions in Formula AI, apply equally to BzF and amino nitrogen bonding positions in Formula I.

In some embodiments of Formula I, x=0.
In some embodiments of Formula I, x=1.
In some embodiments of Formula I, x=2.
In some embodiments of Formula I, x=3.
In some embodiments of Formula I, x=4.
In some embodiments of Formula I, x=5.

In some embodiments of Formula I, x>0 and at least one $R^1$ is an alkyl or deuterated alkyl having 1-20 carbons; in some embodiments, 1-12 carbons; in some embodiments, 3-8 carbons.

In some embodiments of Formula I, x>0 and at least one $R^1$ is a hydrocarbon aryl group having 6-36 ring carbons. The hydrocarbon aryl group can include one or more single ring groups bonded together, one or more fused rings, or combinations thereof.

In some embodiments of Formula I, x>0 and at least one $R^1$ has no heteroaromatic groups.

In some embodiments of Formula I, x>0 and at least one $R^1$ is an amino or deuterated amino group.

In some embodiments of Formula I, x>0 and at least one. $R^1$ has Formula a

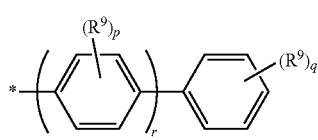

[Formula a]

where:
$R^9$ is the same or different at each occurrence and is selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy, where adjacent $R^9$ groups can be joined together to form an fused aromatic ring or a deuterated fused aromatic ring;

p is the same or different at each occurrence and is an integer from 0-4;
q is an integer from 0-5;
r is an integer from 1 to 5; and
* indicates the point of attachment.

In some embodiments of Formula a, $R^9$ is selected from the group consisting of D, alkyl, hydrocarbon aryl, silyl, germyl, deuterated alkyl, deuterated hydrocarbon aryl, deuterated silyl, and deuterated germyl.

In some embodiments of Formula I, x>0 and at least one $R^1$ has Formula b

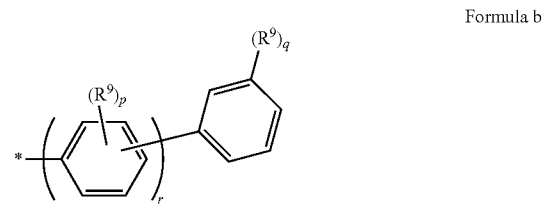

Formula b where $R^9$, p, q, r and * are as in Formula a.

In some embodiments of Formula I, x>0 and at least one $R^1$ is a heteroaryl having at least one ring atom which is selected from the group consisting of N, O, and S.

In some embodiments of Formula I, x>0 and at least one $R^1$ is an N-heteroaryl or deuterated N-heteroaryl having at least one ring atom which is N.

All of the above-described embodiments of N-heteroaryls in Formula AI, apply equally to N-heteroaryls in Formula I.

In some embodiments of Formula I, x>0 and at least one $R^1$ is an S-heteroaryl having at least one ring atom which is S.

All of the above-described embodiments of S-heteroaryls in Formula AI, apply equally to S-heteroaryls in Formula I.

In some embodiments of Formula I, x>0 and at least one $R^1$ is an O-heteroaryl having at least one ring atom that is O.

All of the above-described embodiments of O-heteroaryls in Formula AI, apply equally to O-heteroaryls in Formula I.

In some embodiments of Formula I, x>0 and at least one $R^1$ is an N,O-heteroaryl having at least one ring atom that is N and at least one ring atom that is O.

All of the above-described embodiments of N,O-heteroaryls in Formula AI, apply equally to N,O-heteroaryls in Formula I.

In some embodiments of Formula I, x>0 and at least one is an N,S-heteroaryl having at least one ring atom that is N and at least one ring atom that is S.

All of the above-described embodiments of N,S-heteroaryls in Formula AI, apply equally to N,S-heteroaryls in Formula I.

In some embodiments of Formula I, x>0 and at least one $R^1$ is selected from the group consisting of phenyl, naphthyl, Formula a, and deuterated analogs thereof.

In some embodiments of Formula I, x>0 and at least one $R^1$ has substituents selected from the group consisting of D, F, CN, alkyl, alkoxy, silyl, siloxy, siloxane, germyl, hydrocarbon aryl, heteroaryl, diarylamino, carbazolyl, deuterated alkyl, deuterated alkoxy, deuterated silyl, deuterated siloxy, deuterated siloxane, deuterated germyl, deuterated hydrocarbon aryl, deuterated heteroaryl, deuterated diarylamino, and deuterated carbazolyl.

In some embodiments of Formula I, x>0 and at least one $R^1$ has substituents selected from the group consisting of D, F, CN, alkyl, silyl, germyl, hydrocarbon aryl, deuterated alkyl, deuterated silyl, deuterated germyl, deuterated hydrocarbon aryl, and combinations thereof.

In some embodiments of Formula I, x1=0.
In some embodiments of Formula I, x1=1.
In some embodiments of Formula I, x1=2.
In some embodiments of Formula I, x1=3.
In some embodiments of Formula I, x1=4.
In some embodiments of Formula I, x1=5.
In some embodiments of Formula I, x1>0 and at least one $R^3$ is as described above for $R^1$.
In some embodiments of Formula I, y=0.
In some embodiments of Formula I, y=1.
In some embodiments of Formula I, y=2.
In some embodiments of Formula I, y=3.
In some embodiments of Formula I, y=4.
In some embodiments of Formula I, y=5.
In some embodiments of Formula I, y>0 and at least one $R^2$ is as described above for $R^1$.
In some embodiments of Formula I, y1=0.
In some embodiments of Formula I, y1=1.
In some embodiments of Formula I, y1=2.
In some embodiments of Formula I, y1=3.
In some embodiments of Formula I, y1=4.
In some embodiments of Formula I, y1=5.
In some embodiments of Formula I, y1>0 and at least one $R^4$ is as described above for $R^1$.

In some embodiments of Formula I, the compound has Formula I-a

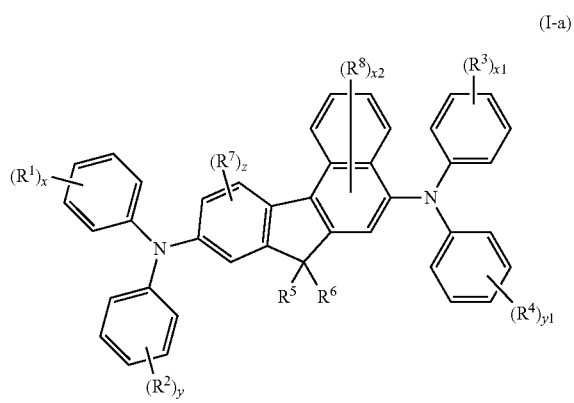

(I-a)

wherein:
$R^1$-$R^4$ are the same or different at each occurrence and are selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy, wherein adjacent groups selected from $R^1$-$R^4$ can be joined together to form a fused ring;

$R^5$ and $R^6$ are the same or different at each occurrence and are selected from the group consisting of alkyl, fluoroalkyl, hydrocarbon aryl, fluoroaryl, and deuterated analogs thereof, where two $R^5$ and $R^6$ alkyl groups can be joined together to make a cycloalkyl ring, and where two $R^5$ and $R^6$ phenyl groups can be joined to form a fluorene group;

$R^7$ and $R^8$ are the same or different at each occurrence and are selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy;

x, x1, x2, y, and y1 are the same or different and are an integer from 0-5; and z is an integer from 0-3;

with the proviso that there is present at least two of $R^1$, two of $R^2$, two of $R^3$, or two of $R^4$ and the at least two groups form a fused ring.

All of the embodiments of $R^1$, $R^2$, $R^3$, $R^4$, $R^5$, $R^6$, $R^7$, $R^8$, x, x1, x2, y, y1, and z described above for Formula I, apply equally to Formula I-a.

In some embodiments of Formula I-a, x=2 and the two $R^1$ groups from a fused 1-naphthyl group.
In some embodiments of Formula I-a, x=2 and the two $R^1$ groups from a fused 2-naphthyl group.
In some embodiments of Formula I-a, y=2 and the two $R^2$ groups from a fused 1-naphthyl group.
In some embodiments of Formula I-a, y=2 and the two $R^2$ groups from a fused 2-naphthyl group.
In some embodiments of Formula I-a, x1=2 and the two $R^3$ groups from a fused 1-naphthyl group.
In some embodiments of Formula I-a, x1=2 and the two $R^3$ groups from a fused 2-naphthyl group.
In some embodiments of Formula I-a, y1=2 and the two $R^4$ groups from a fused 1-naphthyl group.
In some embodiments of Formula I-a, y1=2 and the two $R^4$ groups from a fused 2-naphthyl group.

In some embodiments of Formula I, the compound has Formula I-b

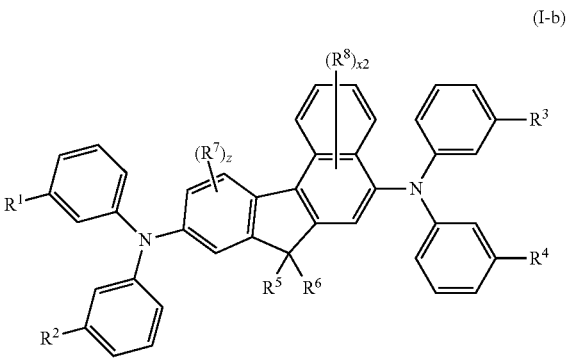

(I-b)

wherein:
$R^1$-$R^4$ are the same or different at each occurrence and are selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy, wherein adjacent groups selected from $R^1$-$R^4$ can be joined together to form a fused ring;

$R^5$ and $R^6$ are the same or different at each occurrence and are selected from the group consisting of alkyl, fluoroalkyl, hydrocarbon aryl, fluoroaryl, and deuterated analogs thereof, where two $R^5$ and $R^6$ alkyl groups can be joined together to make a cycloalkyl ring, and where two $R^5$ and $R^6$ phenyl groups can be joined to form a fluorene group;

$R^7$ and $R^8$ are the same or different at each occurrence and are selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy;

x2 is an integer from 0-5; and z is an integer from 0-3;

with the proviso that at least one of $R^1$-$R^4$ is not D.

All of the embodiments of $R^1$, $R^2$, $R^3$, $R^4$, $R^5$, $R^6$, $R^7$, $R^8$, x2 and z described above for Formula I, apply equally to Formula I-b.

In some embodiments of Formula I-b, two of $R^1$-$R^4$ are not D.

In some embodiments of Formula I-b, three of $R^1$-$R^4$ are not D.

In some embodiments of Formula I-b, all of $R^1$-$R^4$ are not D.

In some embodiments of Formula I-b, $R^1$ is selected from the group consisting of alkyl, silyl, germyl, hydrocarbon aryl, heteroaryl, substituted derivatives thereof, and deuterated analogs thereof. In some embodiments of the substituted derivatives, the substituent groups are selected from the groups consisting of alkyl, silyl, germyl, and deuterated analogs thereof.

In some embodiments of Formula I-b, $R^1$ is an alkyl group having 1-12 carbon atoms or a deuterated analog thereof. In some embodiments, the alkyl group has 1-8 carbon atoms; in some embodiments, 1-6 carbon atoms.

In some embodiments of Formula I-b, $R^1$ is a branched alkyl group having 1-12 carbon atoms or a deuterated analog thereof.

In some embodiments of Formula I-b, $R^1$ is a hydrocarbon aryl having 6-30 ring carbons or a deuterated analog thereof.

In some embodiments of Formula I-b, $R^1$ has Formula a, as described above.

In some embodiments of Formula I-b, $R^1$ is selected from the group consisting of phenyl, naphthyl, biphenyl, and deuterated analogs thereof.

In some embodiments of Formula I-b, $R^1$ is a heteroaryl having 3-30 ring carbons or a deuterated analog thereof.

In some embodiments of Formula I-b, $R^1$ is an N-heteroaryl, as described above.

In some embodiments of Formula I-b, $R^1$ is an O-heteroaryl, as described above.

In some embodiments of Formula I-b, $R^1$ is an S-heteroaryl, as described above.

In some embodiments of Formula I-b, $R^1$ is an N,O-heteroaryl, as described above.

In some embodiments of Formula I-b, $R^1$ is an N,S-heteroaryl, as described above.

All of the above embodiments for $R^1$ in Formula I-b apply equally to $R^2$ in Formula I-b.

All of the above embodiments for $R^1$ in Formula I-b apply equally to $R^3$ in Formula I-b.

All of the above embodiments for $R^1$ in Formula I-b apply equally to $R^4$ in Formula I-b.

Any of the above embodiments of Formula I can be combined with one or more of the other embodiments, so long as they are not mutually exclusive.

Any of the above embodiments of Formula I-a can be likewise combined with one or more of the other embodiments, so long as they are not mutually exclusive.

Any of the above embodiments of Formula I-b can be likewise combined with one or more of the other embodiments, so long as they are not mutually exclusive.

Some non-limiting examples of compounds having Formula AI, Formula AI-a, Formula I, Formula I-a, Formula I-b are shown below.

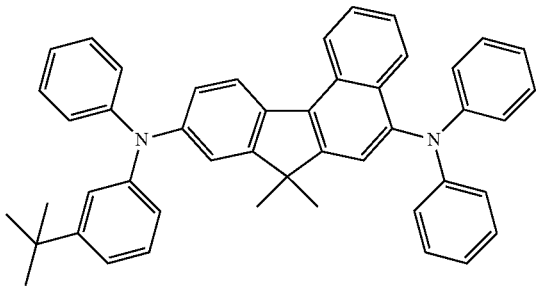

Compound D1

-continued
Compound D2
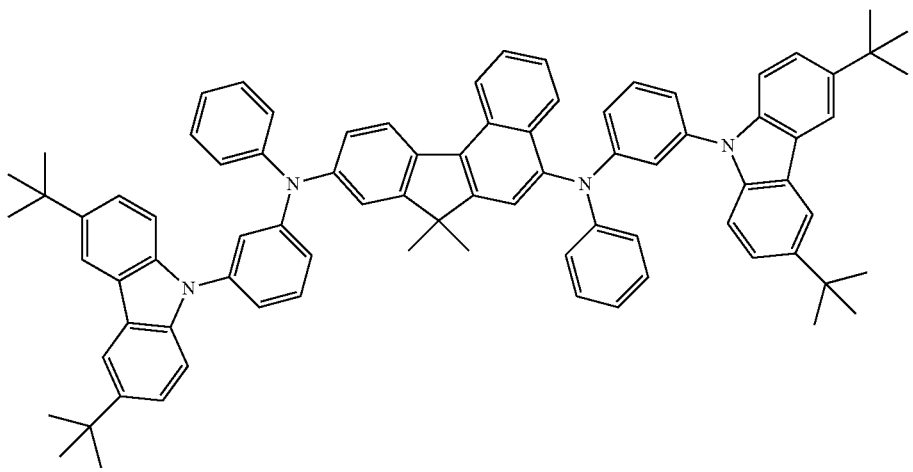
Compound D3
Compound D4
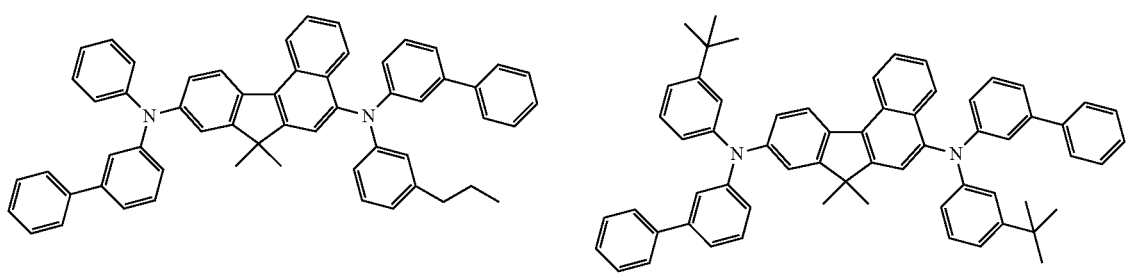
Compound D5
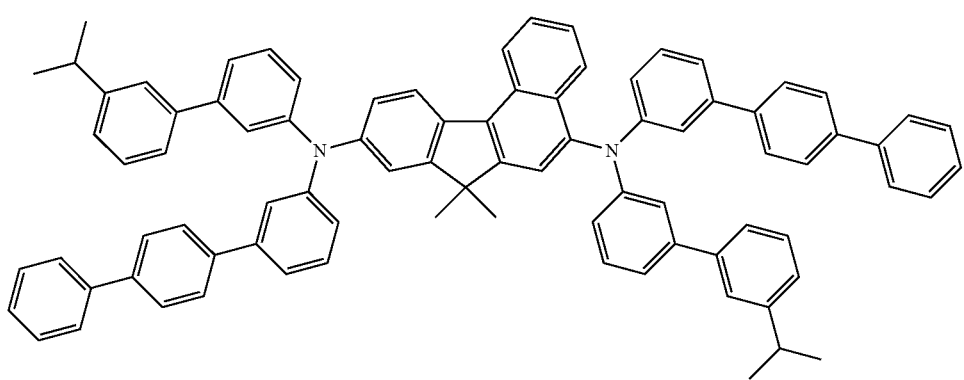
Compound D6
Compound D7
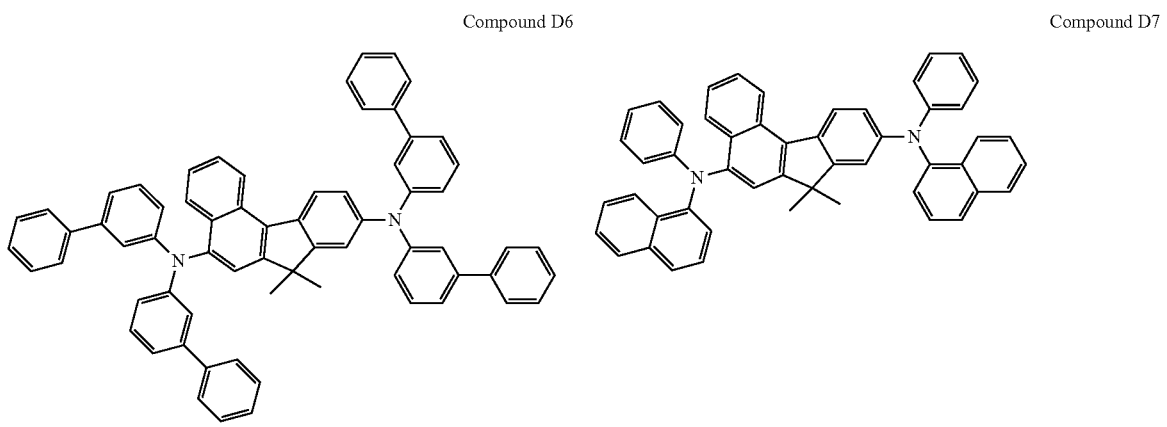

-continued
Compound D8
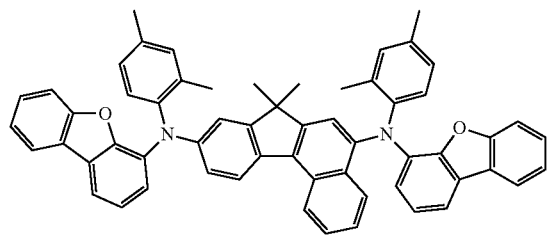
Compound D9
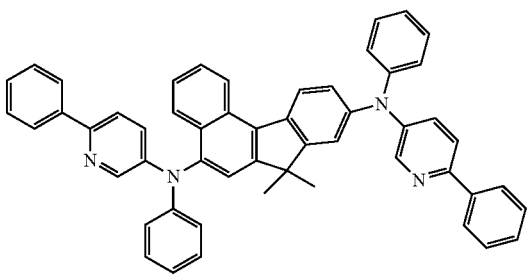
Compound D10
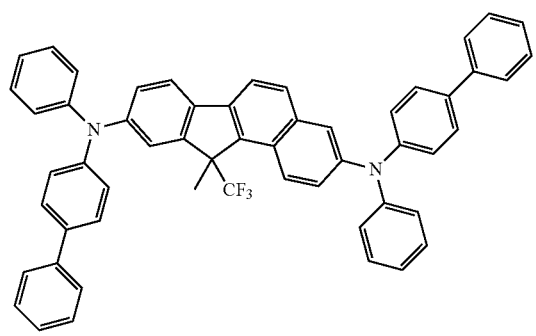
Compound D11
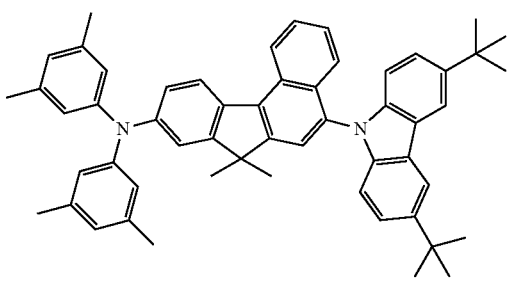
Compound D12
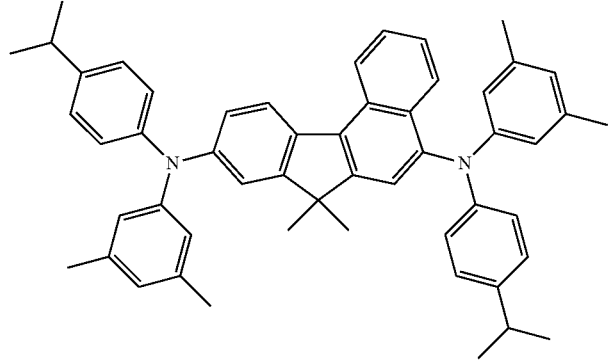
Compound D13
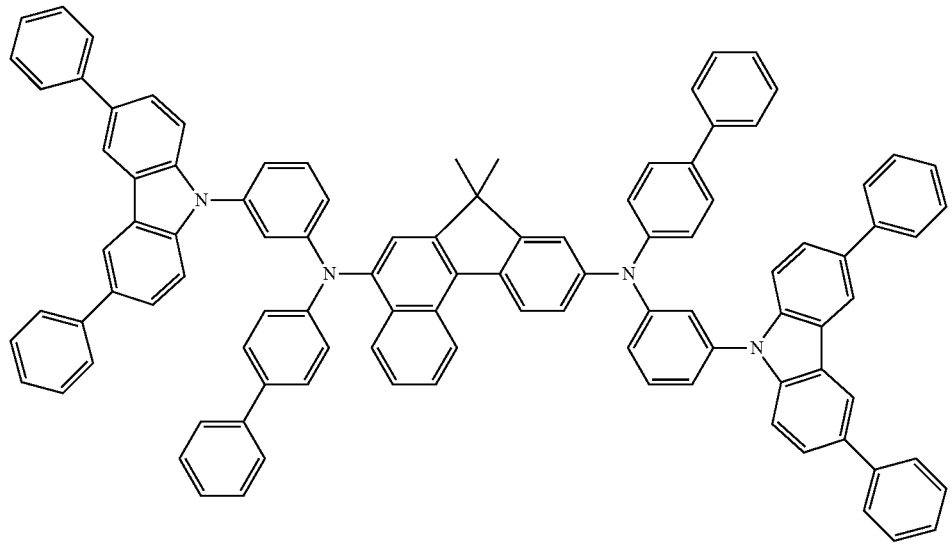

-continued
Compound D14
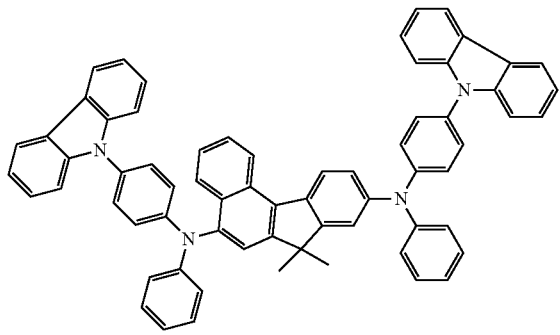
Compound D15
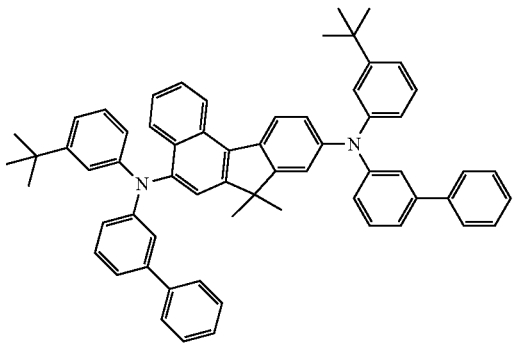
Compound D16
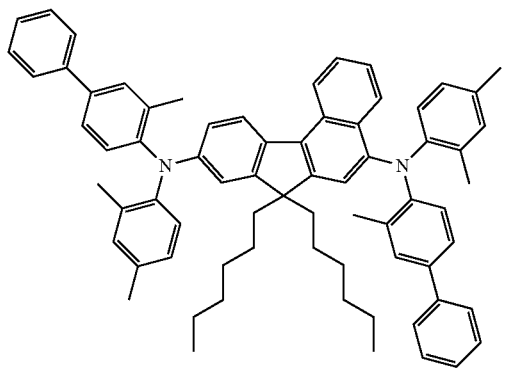
Compound D17
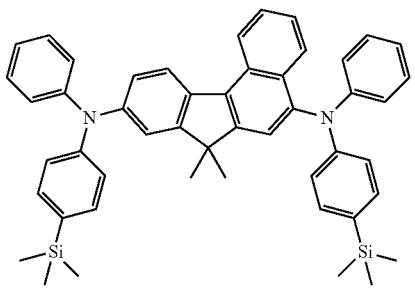
Compound D18
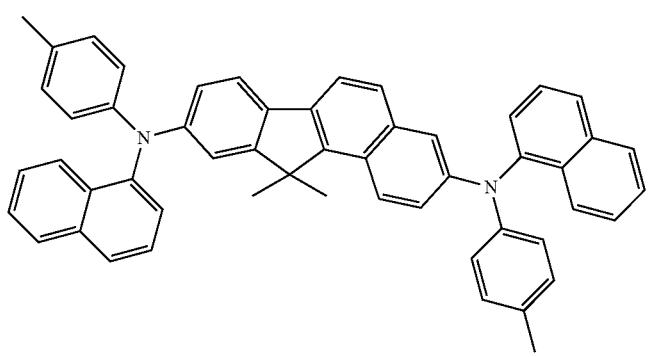
Compound D19
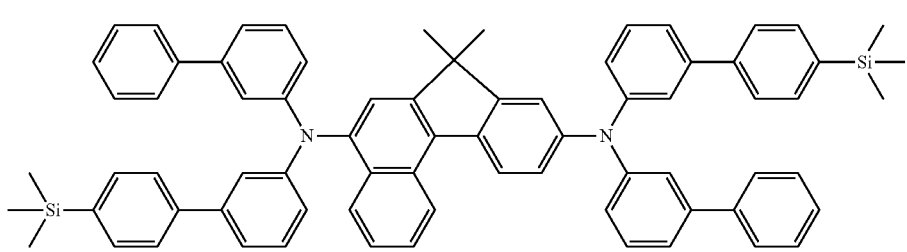

-continued
Compound D20
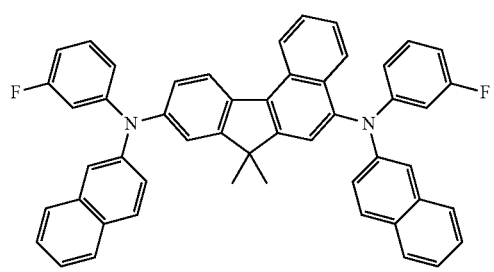
Compound D21
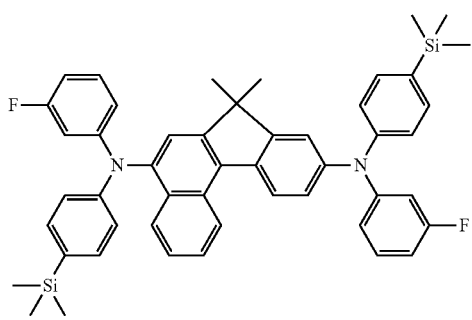
Compound D22
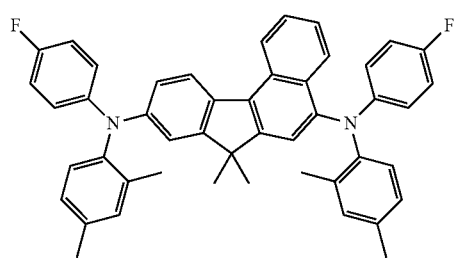
Compound D23
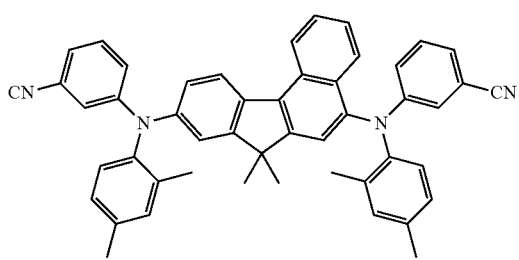
Compound D24
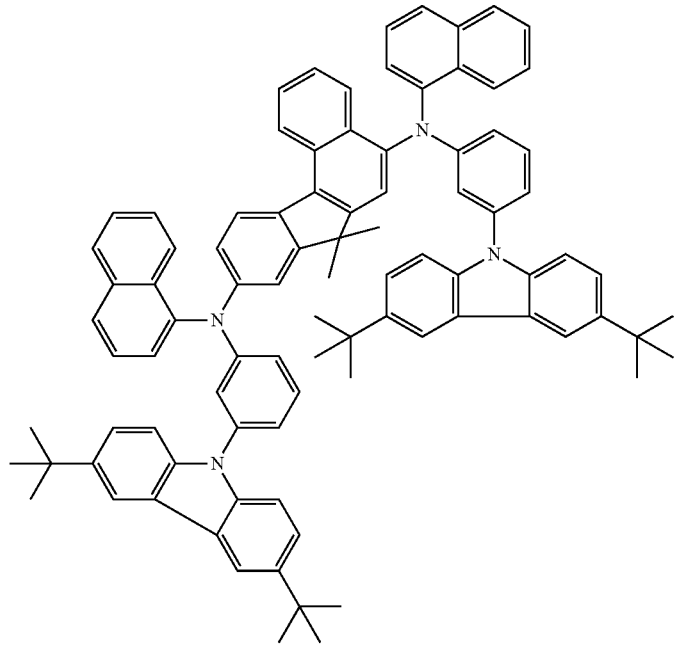

-continued
Compound D25
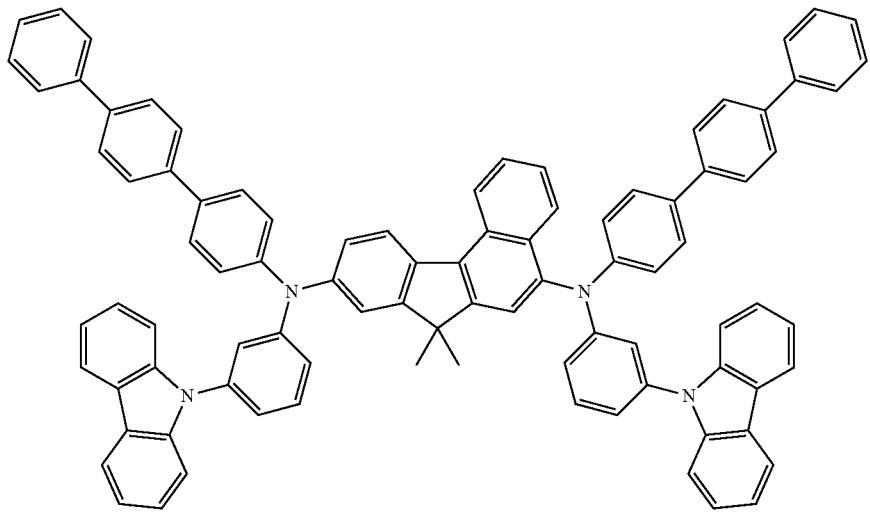
Compound D26
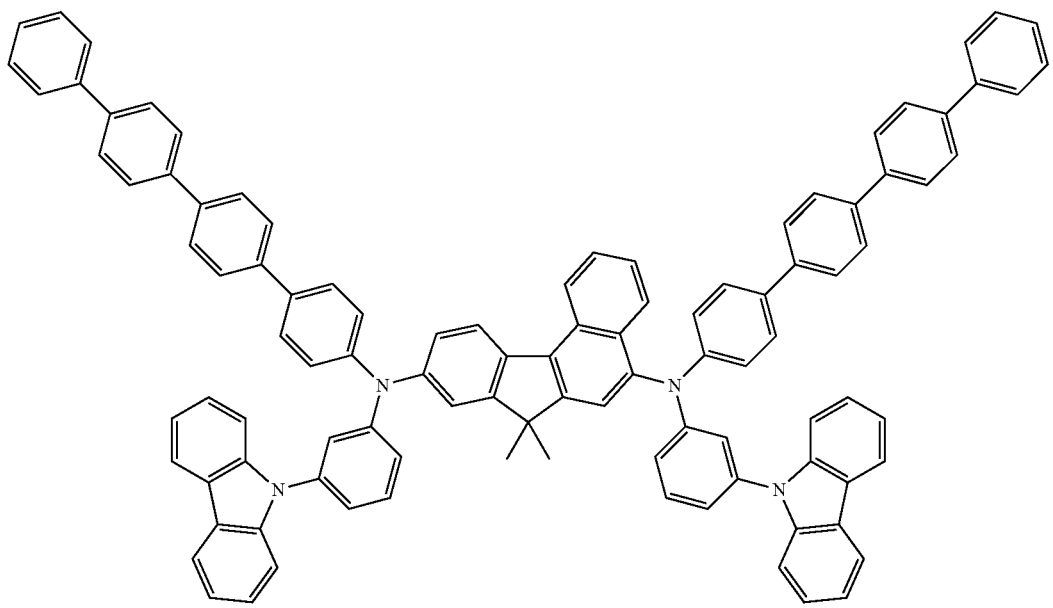
Compound D27
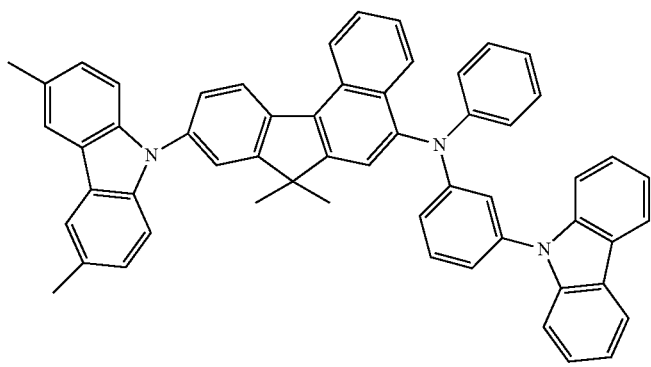

-continued
Compound D28
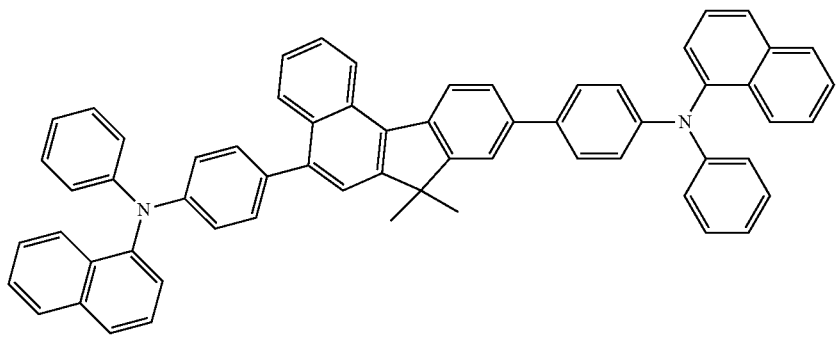
Compound D29
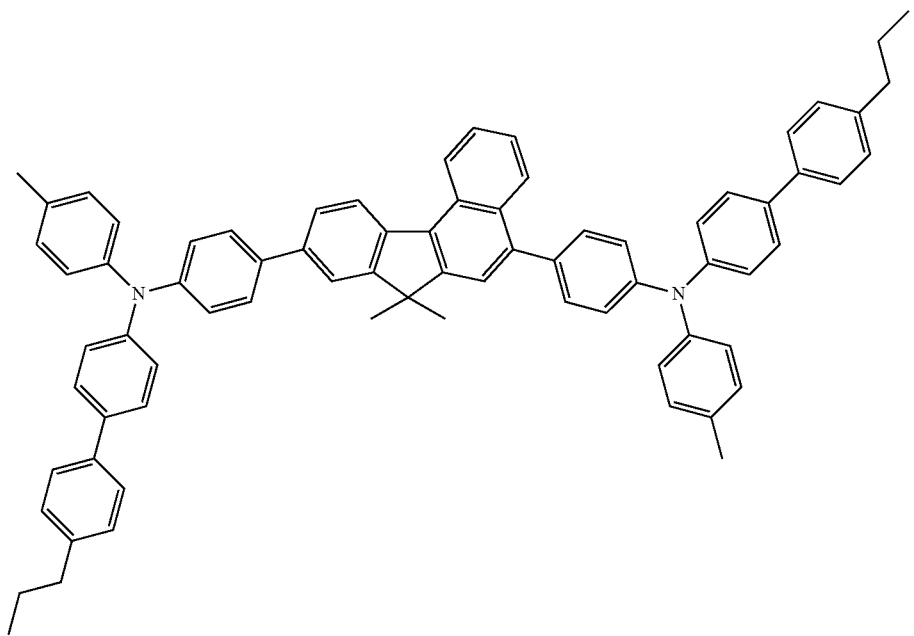
Compound D30
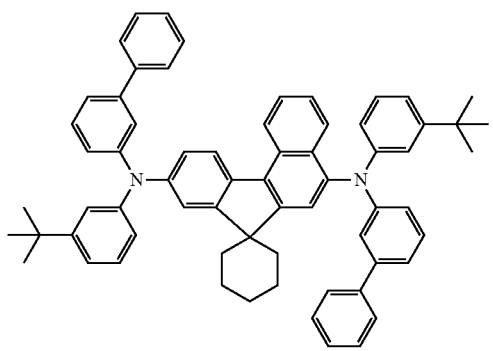
Compound D31

Compound D32

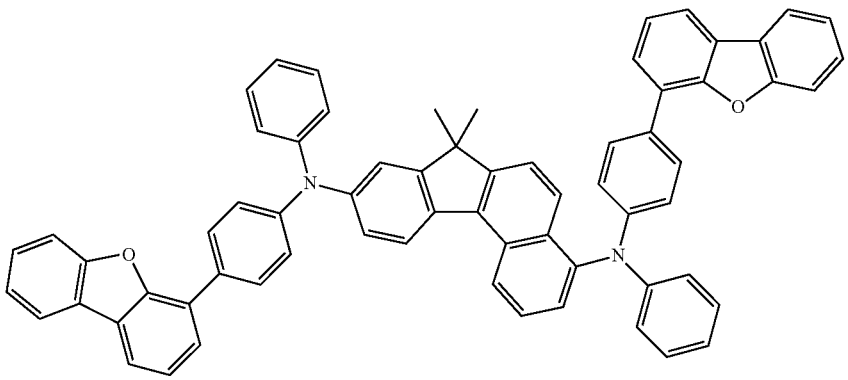

Compound D33

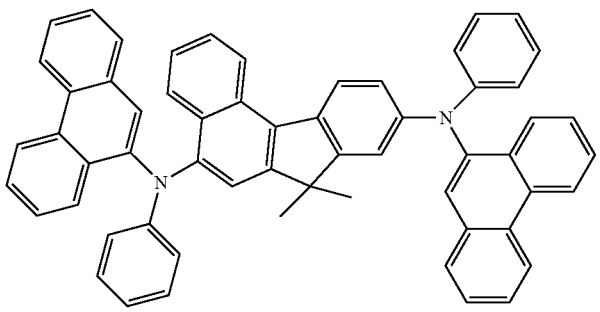

Compounds D1-d through D33-d are the deuterated analogs, having 10-100% deuteration.

(b) Host Material Having Formula II

The host material in the new photoactive composition has Formula II

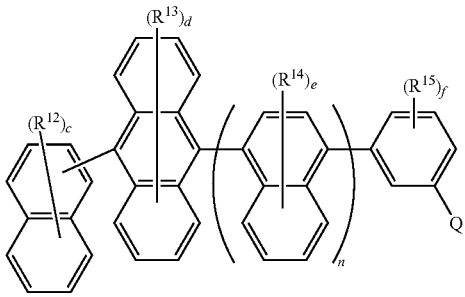

(II)

wherein:
Q is selected from the group consisting of hydrocarbon aryl, heteroaryl, and deuterated analogs thereof;
$R^{12}$-$R^{15}$ are the same or different at each occurrence and are selected from the group consisting of D, F, CN, alkyl, fluoroalkyl, hydrocarbon aryl, fluoroaryl, heteroaryl, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated silyl, deuterated germyl, deuterated alkoxy, deuterated aryloxy, deuterated fluoroalkoxy, deuterated siloxane, and deuterated siloxy;
c is an integer from 0-7;
d is an integer from 0-8;
e is an integer from 0-6;
f is an integer from 0-4; and
n is 0 or 1.

In some embodiments of Formula II, the compound is deuterated. In some embodiments, the compound is at least 10% deuterated; in some embodiments, at least 20% deuterated; in some embodiments, at least 30% deuterated; in some embodiments, at least 40% deuterated; in some embodiments, at least 50% deuterated; in some embodiments, at least 60% deuterated; in some embodiments, at least 70% deuterated; in some embodiments, at least 80% deuterated; in some embodiments, at least 90% deuterated; in some embodiments, 100% deuterated.

In some embodiments of Formula II, deuteration is present on the core anthracene group.

In some embodiments of Formula II, deuteration is present on one or more of aryl groups bonded to the core anthracene.

In some embodiments of Formula II, deuteration is present on one or more of the above positions.

The compounds of Formula II can be made using any technique that will yield a C—C bond. A variety of such techniques are known, such as Suzuki, Yamamoto, Stille, and metal-catalyzed couplings as well as metal catalyzed and oxidative direct arylation.

Deuterated compounds can be prepared in a similar manner using deuterated precursor materials or, more generally, by treating the non-deuterated compound with deuterated solvent, such as benzene-d6, in the presence of a Lewis acid H/D exchange catalyst, such as trifluoromethanesulfonic acid, aluminum trichloride or ethyl aluminum dichloride.

In some embodiments of Formula II, Q is a hydrocarbon aryl group or deuterated aryl group having 6-36 ring carbons. The hydrocarbon aryl group can include one or more single ring groups bonded together, one or more fused rings, or combinations thereof.

In some embodiments of Formula II, Q has no heteroaromatic groups.

In some embodiments of Formula II, Q has no amino groups.

In some embodiments of Formula II, Q has no carbazolyl groups.

In some embodiments of Formula II, Q has Formula a, as described above.

In some embodiments of Formula II, Q has Formula b, as described above.

In some embodiments of Formula II, Q is a hydrocarbon aryl having at least one substituent selected from the group consisting of alkyl, silyl, germyl, and deuterated analogs thereof.

In some embodiments of Formula II, Q is a heteroaryl having at least one ring atom which is selected from the group consisting of N, O, and S.

In some embodiments of Formula II, Q is an N-heteroaryl or deuterated N-heteroaryl having at least one ring atom which is N, as described above.

In some embodiments of Formula II, Q is an S-heteroaryl having at least one ring atom which is S, as described above.

In some embodiments of Formula II, Q is an O-heteroaryl having at least one ring atom that is O, as described above.

In some embodiments of Formula II, Q is an N,O-heteroaryl having at least one ring atom that is N and at least one ring atom that is O, as described above.

In some embodiments of Formula II, Q is an N,S-heteroaryl having at least one ring atom that is N and at least one ring atom that is S, as described above.

In some embodiments of Formula II, Q is a heteroaryl having at least one substituent selected from the group consisting of alkyl, silyl, germyl, and deuterated analogs thereof.

In some embodiments of Formula II, c=0.
In some embodiments of Formula II, c=1.
In some embodiments of Formula II, c=2.
In some embodiments of Formula II, c=3.
In some embodiments of Formula II, c=4.
In some embodiments of Formula II, c=5.
In some embodiments of Formula II, c=6.
In some embodiments of Formula II, c=7.

In some embodiments of Formula II, c>0 and at least one $R^{12}$ is an alkyl or deuterated alkyl having 1-20 carbons; in some embodiments, 1-12 carbons; in some embodiments, 3-8 carbons.

In some embodiments of Formula II, c>0 and at least one $R^{12}$ is a hydrocarbon aryl group having 6-36 ring carbons. The hydrocarbon aryl group can include one or more single ring groups bonded together, one or more fused rings, or combinations thereof.

In some embodiments of Formula II, c>0 and at least one $R^{12}$ has no heteroaromatic groups.

In some embodiments of Formula II, c>0 and at least one $R^{12}$ is an amino or deuterated amino group.

In some embodiments of Formula II, c>0 and at least one $R^{12}$ has Formula a, as described above.

In some embodiments of Formula II, c>0 and at least one $R^{12}$ has Formula b, as described above.

In some embodiments of Formula II, c>0 and at least one $R^{12}$ is a heteroaryl having at least one ring atom which is selected from the group consisting of N, O, and S.

In some embodiments of Formula II, d=0.
In some embodiments of Formula II, d=1.
In some embodiments of Formula II, d=2.
In some embodiments of Formula II, d=3.
In some embodiments of Formula II, d=4.
In some embodiments of Formula II, d=5.
In some embodiments of Formula II, d=6.
In some embodiments of Formula II, d=7.
In some embodiments of Formula II, d=8.

In some embodiments of Formula II, d>0 and at least one $R^{13}$ is as described above for $R^{12}$.

In some embodiments of Formula II, e=0.
In some embodiments of Formula II, e=1.
In some embodiments of Formula II, e=2.
In some embodiments of Formula II, e=3.
In some embodiments of Formula II, e=4.
In some embodiments of Formula II, e=5.
In some embodiments of Formula II, e=6.

In some embodiments of Formula II, e>0 and at least one $R^{14}$ is as described above for $R^{12}$.

In some embodiments of Formula II, f=0.
In some embodiments of Formula II, f=1.
In some embodiments of Formula II, f=2.
In some embodiments of Formula II, f=3.
In some embodiments of Formula II, f=4.

In some embodiments of Formula II, f>0 and at least one $R^{15}$ is as described above for $R^{12}$.

In some embodiments of Formula II, n=0.
In some embodiments of Formula II, n=1.

In some embodiments of Formula II, the compound has Formula II-a

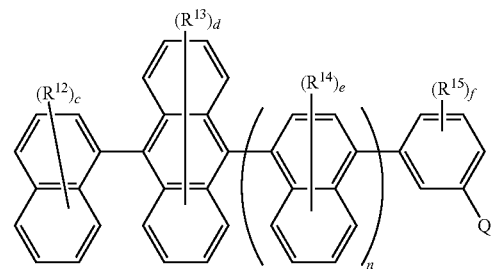

(II-a)

wherein:
  Q is selected from the group consisting of hydrocarbon aryl, heteroaryl, and deuterated analogs thereof;
  $R^{12}$-$R^{15}$ are the same or different at each occurrence and are selected from the group consisting of D, F, CN, alkyl, fluoroalkyl, hydrocarbon aryl, fluoroaryl, heteroaryl, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated silyl, deuterated germyl, deuterated alkoxy, deuterated aryloxy, deuterated fluoroalkoxy, deuterated siloxane, and deuterated siloxy;
  c is an integer from 0-7;
  d is an integer from 0-8;
  e is an integer from 0-6;
  f is an integer from 0-4; and
  n is 0 or 1.

43

All of the embodiments of Q, $R^{12}$, $R^{13}$, $R^{14}$, $R^{15}$, f, and n described above for Formula II, apply equally to Formula II-a.

In some embodiments of Formula II, the compound has Formula II-b

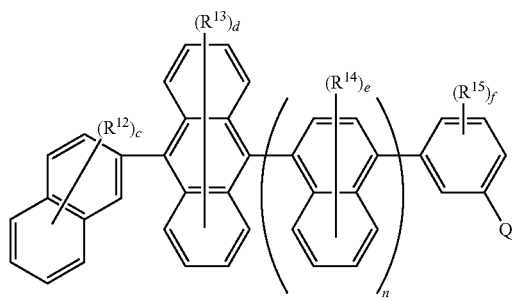

(II-b)

wherein:
- Q is selected from the group consisting of hydrocarbon aryl, heteroaryl, and deuterated analogs thereof;
- $R^{12}$-$R^{15}$ are the same or different at each occurrence and are selected from the group consisting of D, F, CN, alkyl, fluoroalkyl, hydrocarbon aryl, fluoroaryl, heteroaryl, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated silyl, deuterated germyl, deuterated alkoxy, deuterated aryloxy, deuterated fluoroalkoxy, deuterated siloxane, and deuterated siloxy;
- c is an integer from 0-7;
- d is an integer from 0-8;
- e is an integer from 0-6;
- f is an integer from 0-4; and
- n is 0 or 1.

All of the embodiments of Q, $R^{12}$, $R^{13}$, $R^{14}$, $R^{15}$, c, d, e, f, and n described above for Formula II, apply equally to Formula II-b.

Any of the above embodiments of Formula II can be combined with one or more of the other embodiments, so long as they are not mutually exclusive. For example, the embodiment in which n=1 can be combined with the embodiment where Q is phenyl. The same is true for the other non-mutually-exclusive embodiments discussed above. The skilled person would understand which embodiments were mutually exclusive and would thus readily be able to determine the combinations of embodiments that are contemplated by the present application.

Any of the above embodiments of Formula II-a can be likewise combined with one or more of the other embodiments, so long as they are not mutually exclusive.

Any of the above embodiments of Formula II-b can be likewise combined with one or more of the other embodiments, so long as they are not mutually exclusive.

44

Some non-limiting examples of compounds having Formula II are shown below.

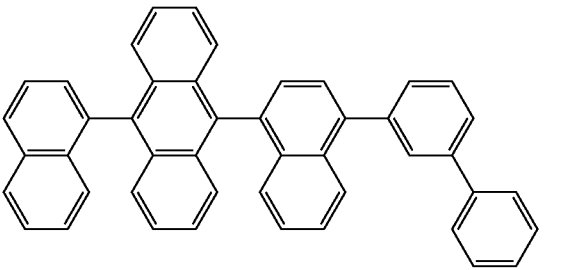

Compound H1

Compound H1-d

Compound H2

Compound H2-d

Compound H3

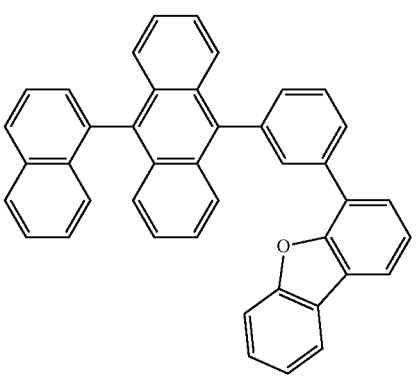

Compound H3-d

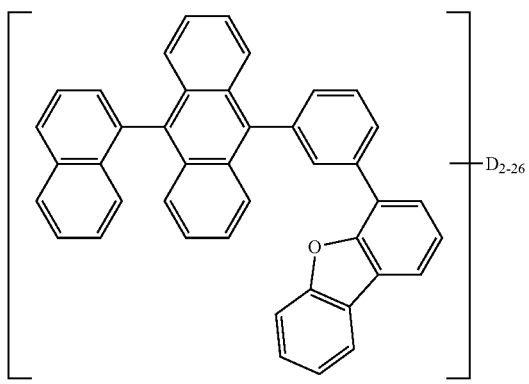

Compound H4

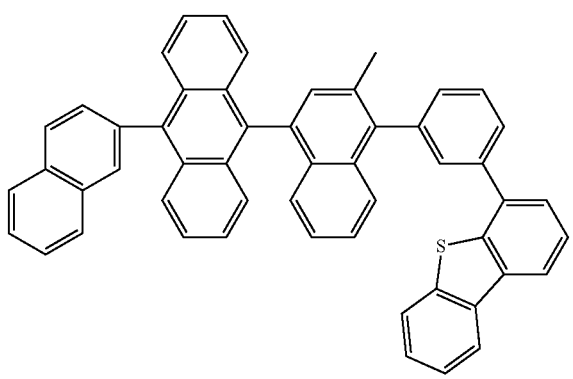

Compound H4-d

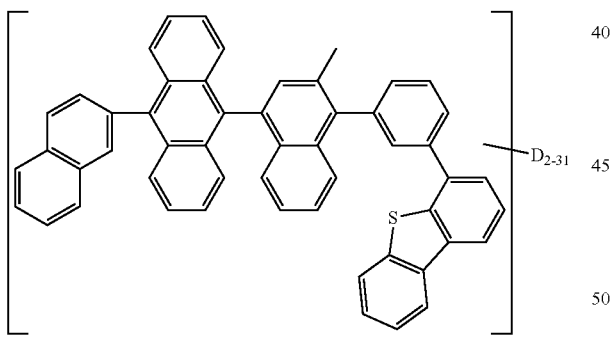

Compound H5

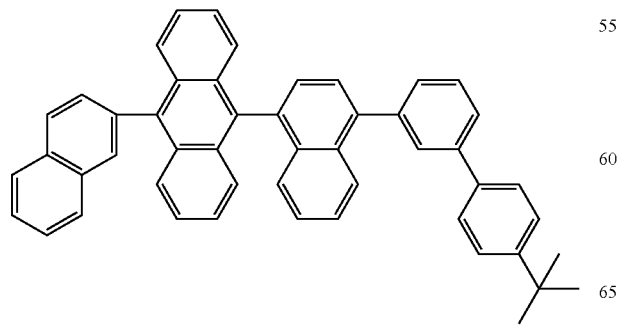

Compound H5-d

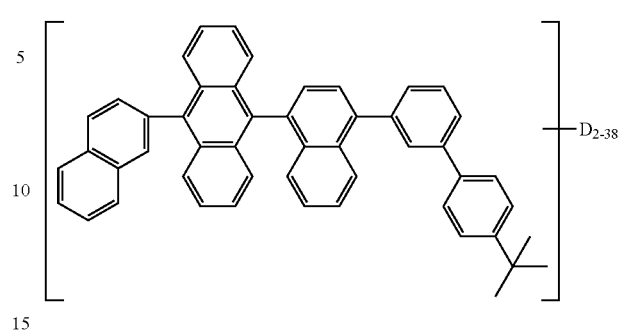

In the photoactive composition, any of the compounds of Formula I represented by the embodiments, specific embodiments, specific examples, and combination of embodiments discussed above can be combined with any of the compounds of Formula II represented by the embodiments, specific embodiments, specific examples, and combination of embodiments discussed above.

3. New Compounds

There are also provided herein new benzofluorene compounds. The new compounds can be used in combination with a host material having Formula II. The new compounds can also be used with a different host material.

(a) Compounds Having Formula III-1, Formula III-2, or Formula III-3

There is provided a new compound having Formula III-1, Formula III-2, or Formula III-3

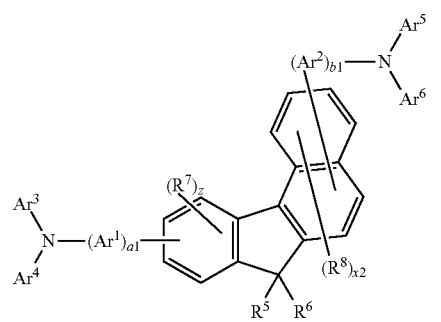

(III-1)

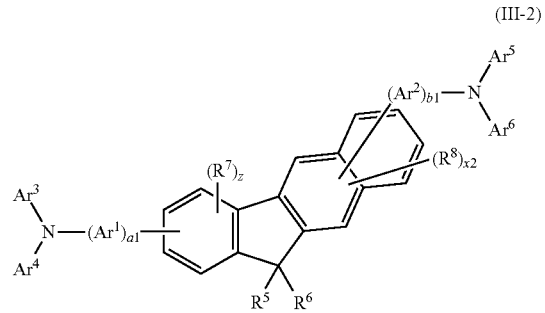

(III-2)

-continued (III-3)

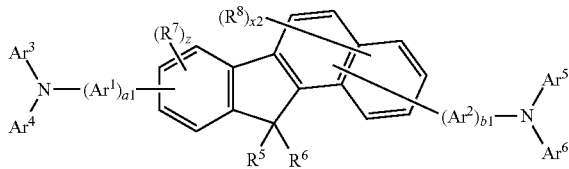

wherein:
$Ar^1$-$Ar^6$ are the same or different and are selected from the group consisting of hydrocarbon aryl, heteroaryl, and deuterated analogs thereof;
$R^5$ and $R^6$ are the same or different at each occurrence and are selected from the group consisting of alkyl, fluoroalkyl, hydrocarbon aryl, fluoroaryl, and deuterated analogs thereof, where two $R^5$ and $R^6$ alkyl groups can be joined together to make a cycloalkyl ring, and where two $R^5$ and $R^6$ phenyl groups can be joined to form a fluorene group;
$R^7$ and $R^8$ are the same or different at each occurrence and are selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy;
a1 and b1 are the same or different and are 0 or 1, with the proviso that a1+b1=1 or 2;
x2 is an integer from 0-5; and
z is an integer from 0-3.

In some embodiments, the compound has Formula III-1.
In some embodiments, the compound has Formula III-2.
In some embodiments, the compound has Formula III-3.
In some embodiments of Formula III-1, Formula III-2, and Formula III-3, a1=1 and b1=0.
In some embodiments of Formula III-1, Formula III-2, and Formula III-3, a1=0 and b1=1.
In some embodiments of Formula III-1, Formula III-2, and Formula III-3, a1=b1=1.

All of the above-described embodiments for $Ar^1$-$Ar^6$, $R^5$-$R^8$, x2 and z in Formula AI apply equally to $Ar^1$-$Ar^6$, $R^5$-$R^8$, x2 and z in Formula III-1, Formula III-2, and Formula III-3.

In some embodiments of Formula III-1, the compound has Formula III-1a (III-1a)

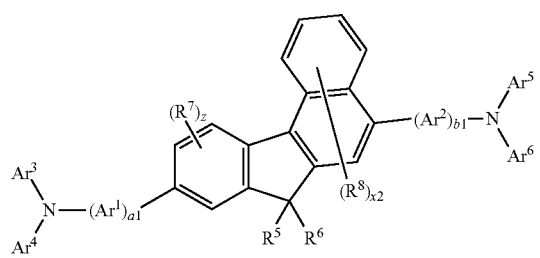

where $Ar^1$-$Ar^6$, $R^5$-$R^8$, a1, b1, x2 and z are as defined above in Formula III-1.

In some embodiments of Formula III-2, the compound has Formula III-2a (III-2a)

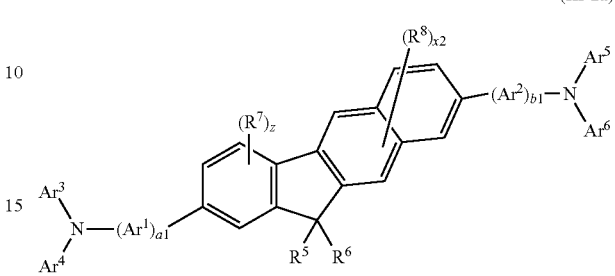

where $Ar^1$-$Ar^6$, $R^5$-$R^8$, a1, b1, x2 and z are as defined above in Formula III-2.

In some embodiments of Formula III-3, the compound has Formula III-3a (III-3a)

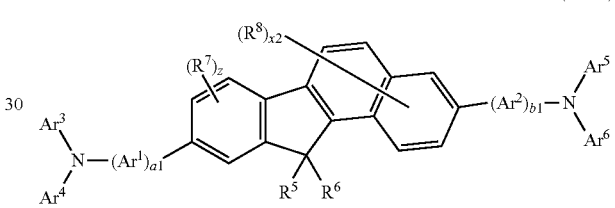

where $Ar^1$-$Ar^6$, $R^5$-$R^8$, a1, b1, x2 and z are as defined above in Formula III-3.

All of the above-described embodiments for $Ar^1$-$Ar^6$, $R^5$-$R^8$, a1, b1, x2 and z in Formula III-1 apply equally to $Ar^1$-$Ar^6$, $R^5$-$R^8$, a1, b1, x2 and z in Formula III-1a, Formula III-2a, and Formula III-3a.

Any of the above embodiments of Formula III-1 can be combined with one or more of the other embodiments, so long as they are not mutually exclusive.

Any of the above embodiments of Formula III-2 can be combined with one or more of the other embodiments, so long as they are not mutually exclusive.

Any of the above embodiments of Formula III-3 can be combined with one or more of the other embodiments, so long as they are not mutually exclusive.

In some embodiments, the compounds having Formula III-1, Formula III-2, and Formula III-3 are used as blue light-emitting dopants in combination with a host material.

Examples of host materials include, but are not limited to, chrysenes, phenanthrenes, triphenylenes, phenanthrolines, naphthalenes, anthracenes, quinolines, isoquinolines, quinoxalines, phenylpyridines, indolocarbazoles, indoloindoles, furans, benzofurans, dibenzofurans, benzodifurans, naphthodifurans, metal quinolinate complexes, substituted derivatives thereof, deuterated analogs thereof, and combinations thereof.

In some embodiments, the host is selected from the group consisting of anthracenes, triphenylenes, anthracenes, indolocarbazoles, indoloindoles, furans, benzofurans, dibenzofurans, benzodifurans, naphthodifurans, substituted derivatives thereof, and deuterated analogs thereof.

In some embodiments, the compounds having Formula III-1, Formula III-2, and Formula III-3 are used as blue light-emitting dopants in combination with a host material having Formula II, as defined above.

(b) Compounds Having Formula IV-1, Formula IV-2, or Formula IV-3

There is provided a new compound having Formula IV-1, Formula IV-2, or Formula IV-3

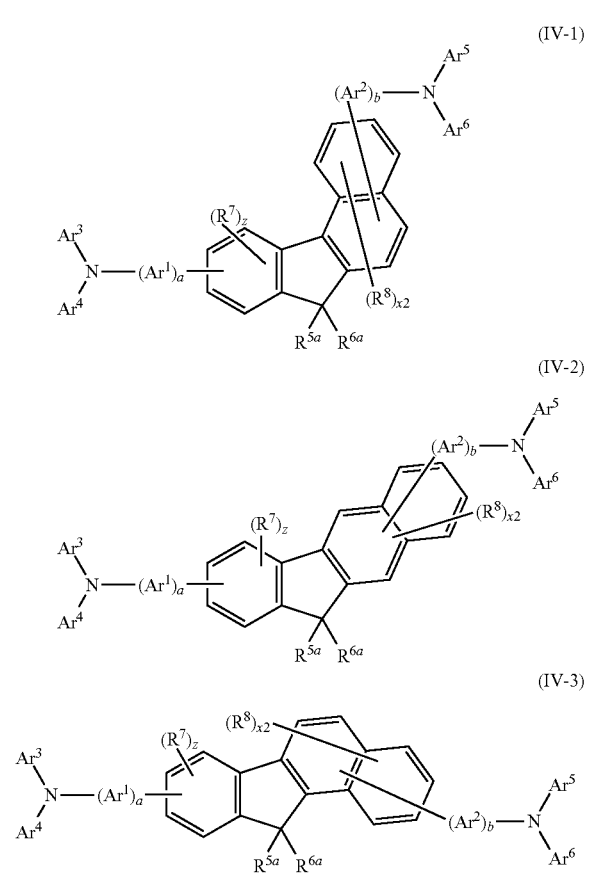

wherein:
$Ar^1$-$Ar^6$ are the same or different and are selected from the group consisting of hydrocarbon aryl, heteroaryl, and deuterated analogs thereof;
$R^{5a}$ and $R^{6a}$ are the same or different at each occurrence and are selected from the group consisting of alkyl, hydrocarbon aryl, and deuterated analogs thereof, where two $R^{5a}$ and $R^{6a}$ alkyl groups can be joined together to make a cycloalkyl ring, and where two $R^{5a}$ and $R^{6a}$ phenyl groups can be joined to form a fluorene group, with the proviso that at least one of $R^{5a}$, $R^{6a}$, the cycloalkyl ring formed from $R^{5a}$ and $R^{6a}$, and the fluorene group formed from $R^{5a}$ and $R^{6a}$ includes at least one electron-withdrawing group;
$R^7$ and $R^8$ are the same or different at each occurrence and are selected from the group consisting of D, F, CN, alkyl, fluoroalkyl, hydrocarbon aryl, fluoroaryl, heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated heteroaryl, deuterated amino, deuterated silyl, deuterated germyl, deuterated alkoxy, deuterated aryloxy, deuterated fluoroalkoxy, deuterated siloxane, and deuterated siloxy;
a and b are the same or different and are 0 or 1;
x2 is an integer from 0-5; and
z is an integer from 0-3.

In some embodiments, the compound has Formula IV-1.
In some embodiments, the compound has Formula IV-2.
In some embodiments, the compound has Formula IV-3.
In some embodiments of Formula IV-1, $R^{5a}$ includes at least one electron-withdrawing group.
In some embodiments, the electron-withdrawing group is selected from the group consisting of fluoro, perfluoroalkyl, and cyano.
In some embodiments, the electron-withdrawing group is selected from the group consisting of fluoro and perfluoroalkyl.
In some embodiments of Formula IV-1, $R^{5a}$ is selected from the group consisting of fluoroalkyl, perfluoroalkyl, and deuterated partially-fluorinated alkyl. In some embodiments, the alkyl has 1-20 carbons; in some embodiments, 1-8 carbons.
In some embodiments of Formula IV-1, $R^{5a}$ is an alkyl having at least one cyano substituent or deuterated analog thereof. In some embodiments, the alkyl has 1-20 carbons; in some embodiments, 1-8 carbons.
In some embodiments of Formula IV-1, $R^{5a}$ is selected from the group consisting of fluoroaryl, perfluoroaryl, and deuterated partially-fluorinated aryl. In some embodiments, the aryl has 6-18 ring carbons; in some embodiments, 6-12 ring carbons.
In some embodiments of Formula IV-1, $R^{5a}$ is a hydrocarbon aryl having at least one cyano substituent or deuterated analog thereof. In some embodiments, the hydrocarbon aryl has 6-18 ring carbons; in some embodiments, 6-12 ring carbons.
In some embodiments of Formula IV-1, $R^{5a}$ is phenyl group having 2-5 fluorines.
In some embodiments of Formula IV-1, $R^{5a}$ is selected from the group consisting of —$CF_3$, —$CH_2CF_3$, $C_6H_3F_2$, and —$C_6F_5$.

All of the above-described embodiments for $R^{5a}$ apply equally to $R^{6a}$.
In some embodiments of Formula IV-1, $R^{5a}$ and $R^{6a}$ are joined together to form a 5-membered aliphatic ring having 1-8 fluorines; in some embodiments, 2-8 fluorines; in some embodiments, 2-5 fluorines.
In some embodiments of Formula IV-1, $R^{5a}$ and $R^{6a}$ are joined together to form a 6-membered aliphatic ring having 1-10 fluorines; in some embodiments, 2-10 fluorines; in some embodiments, 2-6 fluorines.
In some embodiments of Formula IV-1, $R^{5a}$ and $R^{6a}$ are phenyl groups joined together to form a fluorene group having 1-8 fluorines; in some embodiments, 2-8 fluorines; in some embodiments, 4-8 fluorines.
In some embodiments of Formula IV-1, $R^{5a}$=$R^{6a}$.
In some embodiments of Formula IV-1, $R^{5a}$≠$R^{6a}$
In some embodiments of Formula IV-1, $R^{5a}$ is a fluoroalkyl and $R^{6a}$ is an alkyl having no fluorines.
In some embodiments of Formula IV-1, $R^{5a}$ is a fluoroaryl and $R^{6a}$ is an aryl having no fluorines.

All of the above-described embodiments for $R^{5a}$ and $R^{6a}$ in Formula IV-1, apply equally to $R^{5a}$ and $R^{6a}$ in Formula IV-2 and Formula IV-3.

In some embodiments of Formula IV-1, the compound has Formula IV-1a

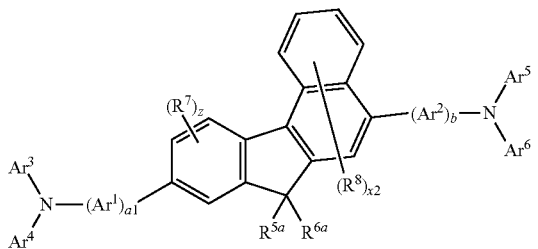

(IV-1a)

where $Ar^1$-$Ar^6$, $R^{5a}$, $R^{6a}$, $R^7$, $R^8$, a, b, x2 and z are as defined above in Formula IV-1.

In some embodiments of Formula IV-2, the compound has Formula IV-2a

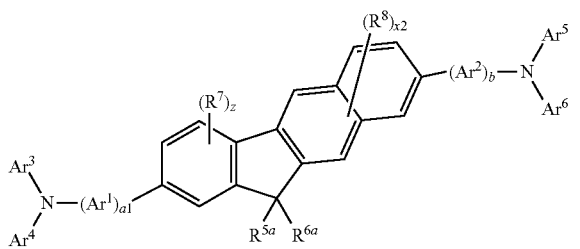

(IV-2a)

where $Ar^1$-$Ar^6$, $R^{5a}$, $R^{6a}$, $R^7$, $R^8$, a, b, x2 and z are as defined above in Formula IV-2.

In some embodiments of Formula IV-3, the compound has Formula IV-3a

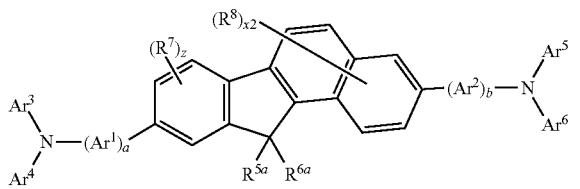

(IV-3a)

where $Ar^1$-$Ar^6$, $R^{5a}$, $R^{6a}$, $R^7$, $R^8$, a, b, x2 and z are as defined above in Formula IV-3.

All of the above-described embodiments for $Ar^1$-$Ar^6$, $R^{5a}$, $R^{6a}$, $R^7$, $R^8$, a, b, x2 and z in Formula IV-1 apply equally to $Ar^1$-$Ar^6$, $R^{5a}$, $R^{6a}$, $R^7$, $R^8$, a, b, x2 and z in Formula IV-1a, Formula IV-2a, and Formula IV-3a.

Any of the above embodiments of Formula IV-1 can be combined with one or more of the other embodiments, so long as they are not mutually exclusive.

Any of the above embodiments of Formula IV-2 can be combined with one or more of the other embodiments, so long as they are not mutually exclusive.

Any of the above embodiments of Formula IV-3 can be combined with one or more of the other embodiments, so long as they are not mutually exclusive.

In some embodiments, the compounds having Formula IV-1, Formula IV-2, and Formula IV-3 are used as blue light-emitting dopants in combination with a host material.

Examples of host materials include, but are not limited to, chrysenes, phenanthrenes, triphenylenes, phenanthrolines, naphthalenes, anthracenes, quinolines, isoquinolines, quinoxalines, phenylpyridines, indolocarbazoles, inoloindoles, furans, benzofurans, dibenzofurans, benzodifurans, metal quinolinate complexes, substituted derivatives thereof, deuterated analogs thereof, and combinations thereof.

In some embodiments, the host is selected from the group consisting of anthracenes, triphenylenes, anthracenes, indolocarbazoles, inoloindoles, furans, benzofurans, dibenzofurans, benzodifurans, substituted derivatives thereof, and deuterated analogs thereof.

In some embodiments, the compounds having Formula IV-1, Formula IV-2, and Formula IV-3 are used as blue light-emitting dopants in combination with a host material having Formula II, as defined above.

4. Devices

Organic electronic devices that may benefit from having one or more layers comprising the new photoactive composition described herein include, but are not limited to, (1) devices that convert electrical energy into radiation (e.g., a light-emitting diode, light emitting diode display, lighting device, luminaire, or diode laser), (2) devices that detect signals through electronics processes (e.g., photodetectors, photoconductive cells, photoresistors, photoswitches, phototransistors, phototubes, IR detectors, biosensors), (3) devices that convert radiation into electrical energy, (e.g., a photovoltaic device or solar cell), and (4) devices that include one or more electronic components that include one or more organic semi-conductor layers (e.g., a transistor or diode).

In some embodiments, the device includes a photoactive layer the new photoactive composition described herein.

In some embodiments, the device includes an anode and a cathode with a photoactive layer therebetween, where the photoactive layer includes the new photoactive composition described herein.

One illustration of an organic electronic device structure which includes the new photoactive composition described herein is shown in FIG. 1. The device 100 has a first electrical contact layer, an anode layer 110 and a second electrical contact layer, a cathode layer 160, and a photoactive layer 140 between them. Adjacent to the anode is a hole injection layer 120. Adjacent to the hole injection layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160. As a further option, devices may have an anti-quenching layer (not shown) between the photoactive layer 140 and the electron transport layer 150.

Layers 120 through 150, and any additional layers between them, are individually and collectively referred to as the active layers.

Figure 2:
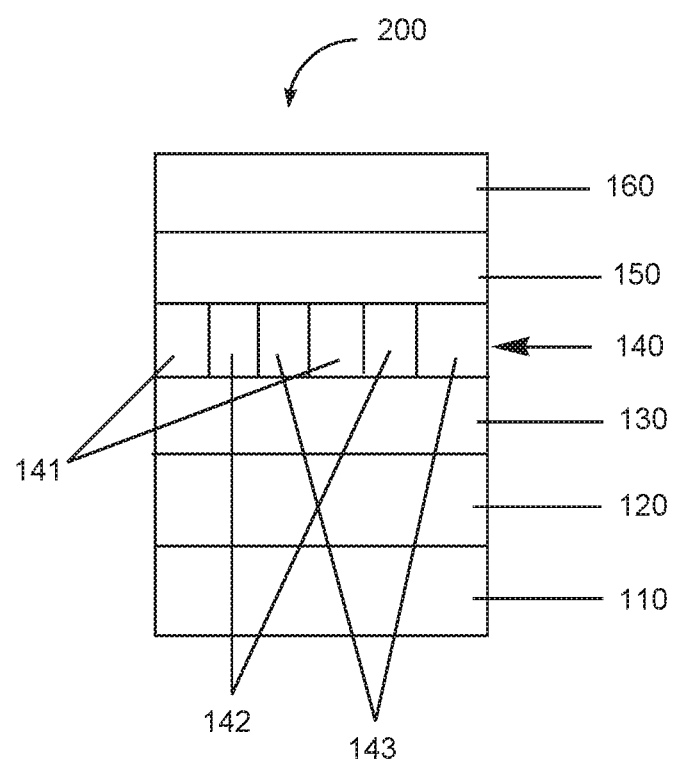
FIG. 2 includes another illustration of an organic light-emitting device including the new photoactive composition described herein.

In some embodiments, the photoactive layer is pixellated, as shown in FIG. 2. In device 200, layer 140 is divided into pixel or subpixel units 141, 142, and 143 which are repeated over the layer. Each of the pixel or subpixel units represents a different color. In some embodiments, the subpixel units are for red, green, and blue. Although three subpixel units are shown in the figure, two or more than three may be used.

In some embodiments, the different layers have the following range of thicknesses: anode 110, 500-5000 Å, in some embodiments, 1000-2000 Å; hole injection layer 120, 50-2000 Å, in some embodiments, 200-1000 Å; hole transport layer 130, 50-2000 Å, in some embodiments, 200-1000 Å; photoactive layer 140, 10-2000 Å, in some embodiments, 100-1000 Å; electron transport layer 150, 50-2000 Å, in some embodiments, 100-1000 Å; cathode 160, 200-10000 Å, in some embodiments, 300-5000 Å. The location of the electron-hole recombination zone in the device, and thus the emission spectrum of the device, can be affected by the relative thickness of each layer. The desired ratio of layer thicknesses will depend on the exact nature of the materials used.

a. Photoactive Layer

In some embodiments, the photoactive layer includes a host material having Formula II and a dopant material having Formula AI. In some embodiments, a second host material is present.

In some embodiments, the photoactive layer includes only a host material having Formula II and a dopant material having Formula AI. In some embodiments, minor amounts of other materials, are present so long as they do not significantly change the function of the layer.

In some embodiments, the photoactive layer includes only a host material having Formula II, a dopant material having Formula AI, and a second host material. In some embodiments, minor amounts of other materials, are present so long as they do not significantly change the function of the layer.

The weight ratio of dopant to total host material is in the range of 2:98 to 50:50; in some embodiments, 3:97 to 30:70; in some embodiments, 5:95 to 20:80.

Examples of second host materials include, but are not limited to, chrysenes, phenanthrenes, triphenylenes, phenanthrolines, naphthalenes, anthracenes, quinolines, isoquinolines, quinoxalines, phenylpyridines, indolocarbazoles, indoloindoles, furans, benzofurans, dibenzofurans, benzodifurans, naphthodifurans, metal quinolinate complexes, substituted derivatives thereof, deuterated analogs thereof, and combinations thereof.

In some embodiments, the second host is selected from the group consisting of triphenylenes, anthracenes, indolocarbazoles, indoloindoles, furans, benzofurans, dibenzofurans, benzodifurans, naphthodifurans, substituted derivatives thereof, and deuterated analogs thereof.

In some embodiments, the weight ratio of host material having Formula II to second host material is in the range of 10:1 to 1:10; in some embodiments 4:1 to 1:4.

In some embodiments, the weight ratio of host material having Formula II to second host material is in the range of 10:1 to 1:1; in some embodiments, 5:1 to 2:1.

In the photoactive layer, any of the compounds of Formula AI represented by the embodiments, specific embodiments, specific examples, and combination of embodiments discussed above can be combined with any of the compounds of Formula II represented by the embodiments, specific embodiments, specific examples, and combination of embodiments discussed above.

b. Other Device Layers

The other layers in the device can be made of any materials which are known to be useful in such layers.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also be made of an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

The hole injection layer 120 includes hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can include charge transfer compounds, and the like, such as copper phthalocyanine and the tetrathiafulvalene-tetracyanoquinodimethane system (TTF-TCNQ).

In some embodiments, the hole injection layer includes at least one electrically conductive polymer and at least one fluorinated acid polymer.

In some embodiments, the hole injection layer is made from an aqueous dispersion of an electrically conducting polymer doped with a colloid-forming polymeric acid. Such materials have been described in, for example, published U.S. patent applications US 2004/0102577, US 2004/0127637, US 2005/0205860, and published PCT application WO 2009/018009.

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino) phenyl]cyclohexane (TAPC), N,N'-bis(4-methylphenyl)-N,N'-bis(4-ethylphenyl)-[1,1'-(3,3'-dimethyl) biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (□-NPB), and porphyrinic compounds, such as copper phthalocyanine. In some embodiments, the hole transport layer includes a hole transport polymer. In some embodiments, the hole transport polymer is a distyrylaryl compound. In some embodiments, the aryl group has two or more fused aromatic rings. In some embodiments, the aryl group is an acene. The term "acene" as used herein refers to a hydrocarbon parent component that contains two or more ortho-fused benzene rings in a straight linear arrangement. Other commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable.

In some embodiments, the hole transport layer further includes a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

In some embodiments, more than one hole transport layer is present (not shown).

Examples of electron transport materials which can be used for layer 150 include, but are not limited to, metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butyl-phenyl)-1,3,4-oxadiazole (PBD), 3-(4-biphenylyl)-4-phenyl-5-(4-t-butylphenyl)-1,2,4-triazole (TAZ), and 1,3,5-tri (phenyl-2-benzimidazole)benzene (TPBI); quinoxaline derivatives such as 2,3-bis(4-fluorophenyl)quinoxaline; fluoranthene derivatives, such as 3-(4-(4-methylstyryl)phenyl-p-tolylamino)fluoranthene; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport layer further includes an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

In some embodiments, an anti-quenching layer may be present between the photoactive layer and the electron transport layer to prevent quenching of blue luminance by the electron transport layer. To prevent energy transfer quenching, the singlet energy of the anti-quenching material has to be higher than the singlet energy of the blue emitter. To prevent electron transfer quenching, the LUMO level of the anti-quenching material has to be shallow enough (with respect to the vacuum level) such that electron transfer between the emitter exciton and the anti-quenching material is endothermic. Furthermore, the HOMO level of the anti-quenching material has to be deep enough (with respect to the vacuum level) such that electron transfer between the emitter exciton and the anti-quenching material is endothermic. In general, anti-quenching material is a large band-gap material with high singlet and triplet energies.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

Alkali metal-containing inorganic compounds, such as LiF, CsF, $Cs_2O$ and $Li_2O$, or Li-containing organometallic compounds can also be deposited between the organic layer 150 and the cathode layer 160 to lower the operating voltage. This layer, not shown, may be referred to as an electron injection layer.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

c. Device Fabrication

The device layers can be formed by any deposition technique, or combinations of techniques, including vapor deposition, liquid deposition, and thermal transfer.

In some embodiments, the photoactive layer is fabricated by vapor deposition.

In some embodiments, the photoactive layer is fabricated by liquid deposition.

In some embodiments, the device is fabricated by vapor deposition of layers. Vapor deposition methods are well known in the art.

In some embodiments, the device is fabricated by liquid deposition of the hole injection layer, the hole transport layer, and the photoactive layer, and by vapor deposition of the anode, the electron transport layer, an electron injection layer and the cathode.

The hole injection layer can be deposited from any liquid medium in which it is dissolved or dispersed and from which it will form a film. In some embodiments, the liquid medium includes only one or more organic solvents. In some embodiments, minor amounts of other materials are present, so long as they do not substantially affect the liquid medium.

In some embodiments, the liquid medium includes only water or includes only water and an organic solvent. In some embodiments, minor amounts of other materials are present, so long as they do not substantially affect the liquid medium.

The hole injection material is present in the liquid medium in an amount from 0.5 to 10 percent by weight.

In some embodiments, the hole injection layer is formed by any continuous or discontinuous liquid deposition technique. In some embodiments, the hole injection layer is applied by spin coating. In some embodiments, the hole injection layer is applied by ink jet printing. In some embodiments, the hole injection layer is applied by continuous nozzle printing. In some embodiments, the hole injection layer is applied by slot-die coating. After liquid deposition, the liquid medium can be removed in air, in an inert atmosphere, or by vacuum, at room temperature or with heating.

In some embodiments, the hole transport layer is formed by liquid deposition of hole transport material in a liquid medium. The liquid medium is one in which the hole transport material is dissolved or dispersed and from which it will form a film. In some embodiments, the liquid medium includes one or more organic solvents. In some embodiments, the liquid medium includes water or water and an organic solvent. In some embodiments, the organic solvent is an aromatic solvent. In some embodiments, the organic liquid is selected from chloroform, dichloromethane, chlorobenzene, dichlorobenzene, toluene, xylene, mesitylene, anisole, and mixtures thereof. The hole transport material can be present in the liquid medium in a concentration of 0.2 to 2 percent by weight. The hole transport layer can be applied by any continuous or discontinuous liquid deposition technique. In some embodiments, the hole transport layer is applied by spin coating. In some embodiments, the hole transport layer is applied by ink jet printing. In some embodiments, the hole transport layer is applied by continuous nozzle printing. In some embodiments, the hole transport layer is applied by slot-die coating. After liquid deposition, the liquid medium can be removed in air, in an inert atmosphere, or by vacuum, at room temperature or with heating.

In some embodiments, the photoactive layer is formed by vapor deposition. Such techniques are well known in the art.

In some embodiments, the photoactive layer is formed by liquid deposition of the photoactive material and one or more host materials in a liquid medium. The liquid medium is one in which the materials of the photoactive layer are dissolved or dispersed and from which it will form a film. In some embodiments, the liquid medium includes one or more organic solvents. In some embodiments, minor amounts of additional materials are present so long as they do not substantially affect the function of the photoactive layer.

Suitable classes of solvents include, but are not limited to, aliphatic hydrocarbons (such as decane, hexadecane, and decalin), halogenated hydrocarbons (such as methylene chloride, chloroform, chlorobenzene, benzotrifluoride, and perfluoroheptane), aromatic hydrocarbons (such as non-substituted and alkyl- and alkoxy-substituted benzenes, toluenes and xylenes), aromatic ethers (such as anisole, dibenzyl ether, and fluorinated derivatives), heteroaromatics (such as pyridine) polar solvents (such as tetrahydropyran, dimethylacetamide, N-methyl pyrrolidone, and nitriles such as acetonitrile), esters (such as ethylacetate, propylene carbonate, methyl benzoate, and phosphate esters such as tributyl-phosphate), alcohols and glycols (such as isopropanol and ethylene glycol), glycol ethers and derivatives (such as propylene glycol methyl ether and propylene glycol methyl ether acetate), and ketones (such as cyclopentanone and diisobutyl ketone).

The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In some embodiments, the photoactive layer is applied by spin coating. In some embodiments, the photoactive layer is applied by ink jet printing. In some embodiments, the photoactive layer is applied by continuous nozzle printing. In some embodiments, the photoactive layer is applied by slot-die coating. After liquid deposition, the liquid medium can be removed in air, in an inert atmosphere, or by vacuum, at room temperature or with heating.

The electron transport layer can be deposited by any vapor deposition method. In some embodiments, it is deposited by thermal evaporation under vacuum.

The electron injection layer can be deposited by any vapor deposition method. In some embodiments, it is deposited by thermal evaporation under vacuum.

The cathode can be deposited by any vapor deposition method. In some embodiments, it is deposited by thermal evaporation under vacuum.

EXAMPLES

Synthesis Example 1

This example illustrates the preparation of dibromobenzofluorene intermediates.

a. Synthesis of Benzofluorene Core Materials 48C1 (Core BzF-2) and 48C2 (Core BzF-3)

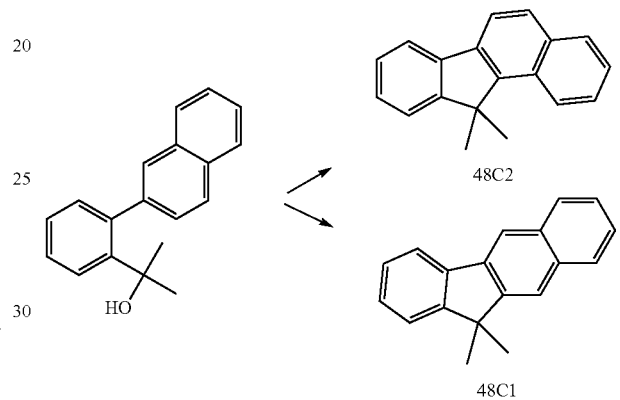

Trifluoroacetic acid (431 g, 2.265 mol) and dichloromethane, 890 mL were combined and sparged with nitrogen. Added 37.2 g of Cmpd 48B from above in 170 mL dichloromethane dropwise over an hour. 50% NaOH solution was slowly added to neutralize the acid. The organic layer was separated and preabsorbed onto 136 grams of silica. Performed column chromatography with a 4"×10" silica column with 100% hexanes followed by 1% DCM in hexanes increasing gradient to 4% DCM in hexanes. The leading spot of four was the intended product concentrated to 21.5 grams (61%) of white solid as a mixture of Cmpds 48C1 and 48C2.

b. Synthesis of dibromo-7,7-dimethyl-7H-benzofluorenes

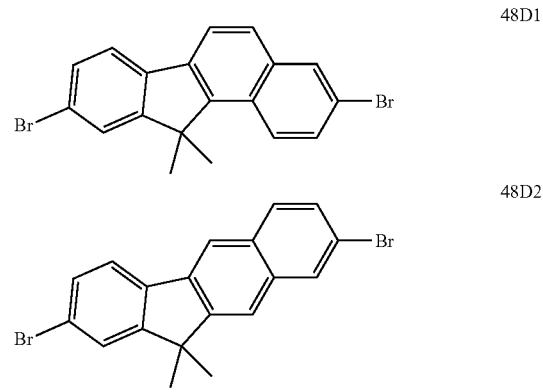

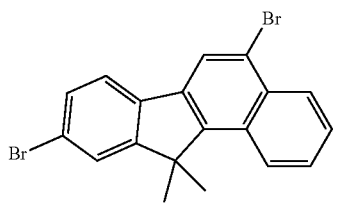

A mixture of cmpds 48C1 and 48C2 above (9.68 g, 0.0396 mol), 80 mL dichloromethane, 55 mL acetic acid and zinc chloride (13.66 g, 0.1 mol) was stirred and cooled to −6° C. A solution of 150 mL dichloromethane, 5 mL acetic acid and trimethylammonium benzyltribromide (34.11 g, 0.0396 mol) was added dropwise over 90 minutes. A further 20 mL dichloromethane and acetic acid, 20 mL was added to the pot during the addition. The reaction was stirred overnight and slowly warmed to ambient temperature. Sodium hydrogen sulfite was added until the color was eliminated and the solution was then evaporated to dryness. The solid was partitioned with dichloromethane and water and neutralized with potassium carbonate. The organic layer was concentrated to 17.8 g of brown solid which was pre-absorbed from DCM onto 35 g of silica gel and then chromatographed on silica eluting with hexanes. The first fraction, was concentrated to 9.4 g white solid which was a mixture of compounds 48D1, 48D2, and 48D3-rich in compound 48D1, while the second fraction was concentrated to 4.6 grams white solid which was pure 48D3 (core BzF-3) (confirmed by x-ray single crystallography). Compounds 48D1 (core BzF-3) and 48D2 (core BzF-2) can be isolated by careful chromatography of the mixture (compounds 48D1, 48D2, and 48D3) using hexane eluent on a silica gel column.

The compound 5,9-dibromo-7,7-dimethyl-7H-benzo[c]fluorene (core BzF-1), is available commercially.

Synthesis Example 2

This example illustrates the preparation of benzofluorene compounds having Formula A1.

The compounds are generally prepared by reacting a dibromobenzofluorene with a secondary amine.

a. Secondary Amine

The desired secondary amine can be prepared according to the scheme below:

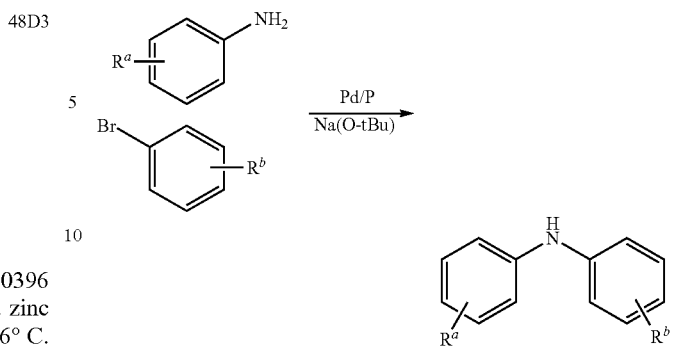

where $R^a$ and $R^b$ represent the desired substituents.

Equimolar amounts of the appropriate aniline and bromoaryl can be reacted in toluene at 70 C with 1 mol equivalent of sodium t-butoxide for 2-4 hrs using a catalyst of Pd2(DBA)3:P(t-Bu)3 1:2 at a 1 mol % ratio to the reagents. The resulting solution can be evaporated, chromatographed with toluene eluent through alumina plug and the secondary amine isolated by evaporation and addition of methanol. The bromides and anilines for the sec amines are generally commercially available.

Another synthetic scheme is show below:

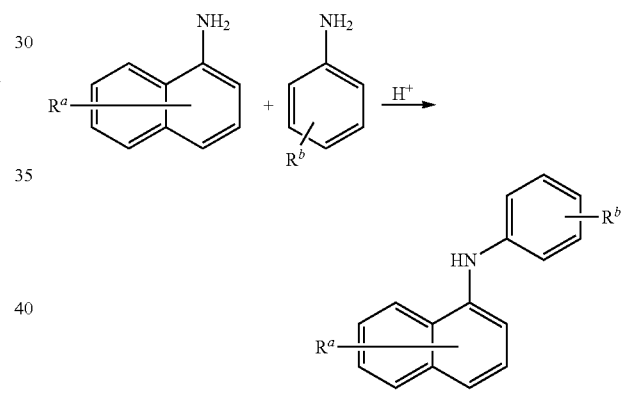

b. Benzofluorene Compound

Compound D6 can be made according to the following scheme:

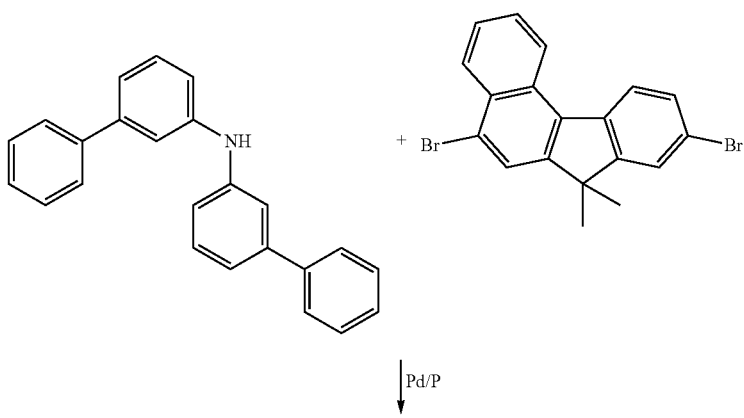

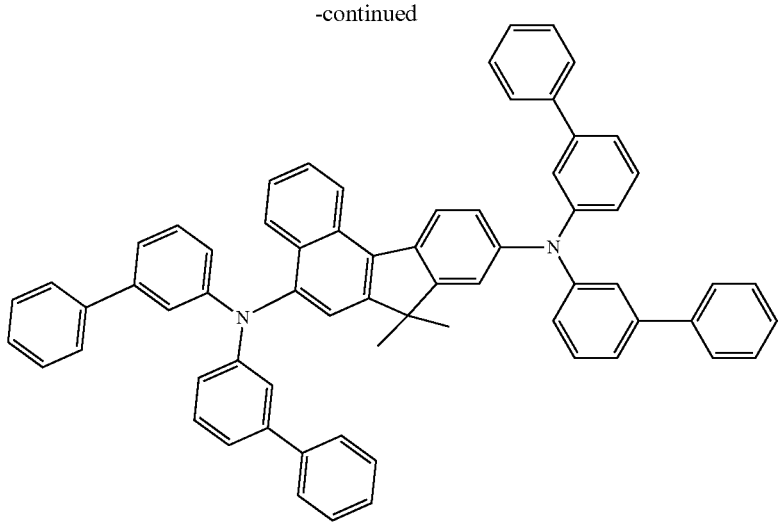

One mol equivalent of dibromobenzofluorene and 2 mol equivalents of the secondary amine can be reacted in toluene with 2 mol equivalents of sodium t-butoxide for 8-10 hrs using a catalyst of $Pd_2(DBA)_3:P(t-Bu)_3$ 1:2 at a 1 mol % ratio to the reagents. The resulting solution can be evaporated, chromatographed with 1:3 chloroform in hexanes through alumina plug. The fractions can be dried and precipitated from dichloromethane into methanol to obtain Compound D6.

Synthesis Example 3

This example illustrates the preparation of a compound having Formula IA, Compound D10.

a. 3,9-dibromo-11-methyl-11-(trifluoromethyl)benzo[a]fluorene

The dibromo intermediate compound was prepared according to the following scheme.

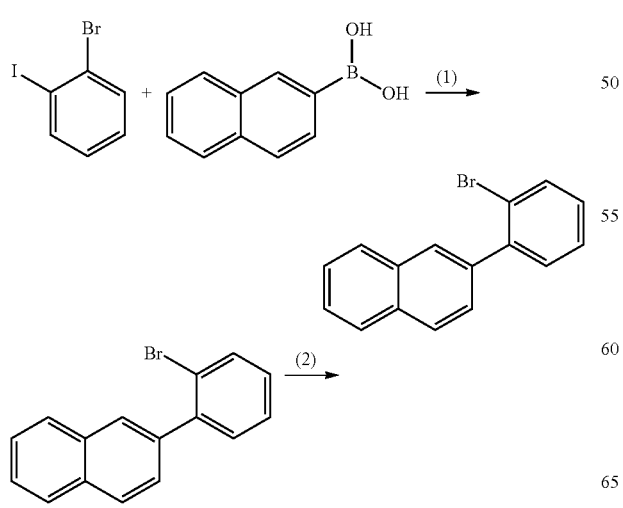

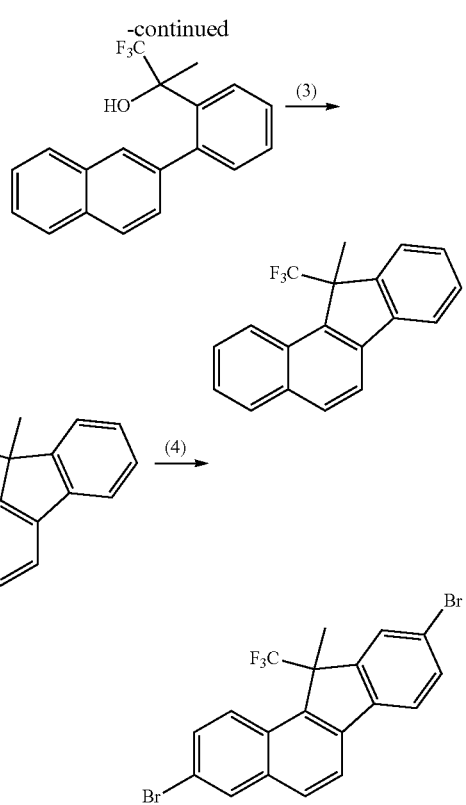

(1) In step (1), the two reactants were combined with $Pd(PPh_3)_4$, 2M $Na_2CO_3$, and aliquat-336 in toluene, and heated at 80° C. for 16 h.

(2) The product of step (1) was then combined with 1,1,1-trifluoroacetone in THF and cooled to −78° C. To this was added n-butyllithium and the mixture allowed to warm to room temperature with stirring for 16 h.

(3) The product of step (2) was combined with methanesulfonic acid in dichloromethane at 0° C. and allowed to warm to room temperature with stirring for 32 h.

(4) The product of step (3) was treated with Br2 in dichloromethane at 0° C. and allowed to warm to room temperature with stirring for 32 h, to obtain 3,9-dibromo-11-methyl-11-(trifluoromethyl)benzo[a]fluorene.

b. Compound D10

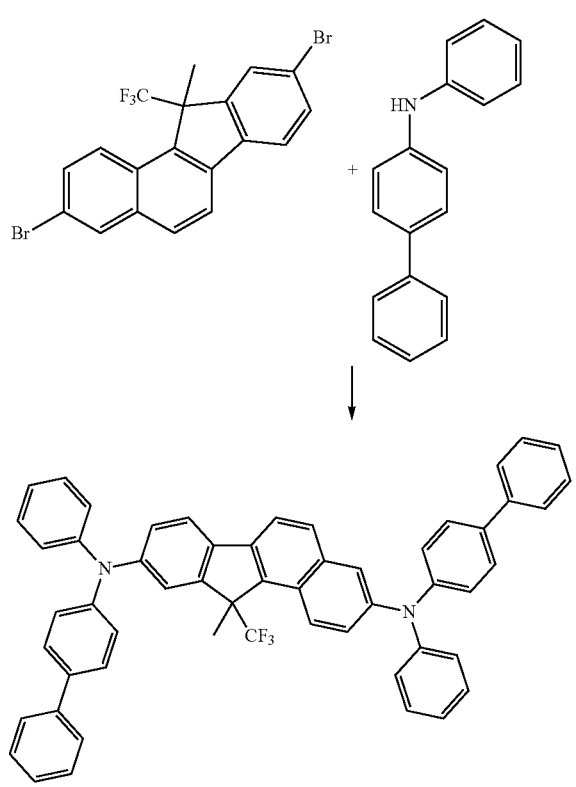 [SMILES: CC1(C(F)(F)F)c2cc(Br)ccc2-c2ccc3cc(Br)ccc3c21 ; [C+]1=CC(c2ccccc2)=CC=C1Nc1ccccc1 ; CC1(C(F)(F)F)c2cc(N(c3ccccc3)c3ccc(-c4ccccc4)cc3)ccc2-c2ccc3cc(N(c4ccccc4)c4ccc(-c5ccccc5)cc4)ccc3c21]

Pd2/DBA (0.0183 g, 0.0197 mmol), tri-t-butylphosphine (0.0090 g, 0.0445 mmol), sodium-t-butoxide (0.18 g, 1.873 mol), 10.0 ml toluene, 3,9-dibromo-11-methyl-11-(trifluoromethyl)benzo[a]fluorene (0.2026 g, 0.444 mmol), and [1,1'-biphenyl]-4-amine, N-phenyl-(0.2396 g, 0.977 mmol) were combined in a drybox. The mixture was heated at 100° C. for 2.75 hours. The reaction mixture was preabsorbed to 0.9 grams of silica and eluted through silica with toluene in hexanes. Product cuts were concentrated, recrystallized from toluene and acetonitrile and then from toluene and methanol for 125 mg (35% yield) of 99.7% pure product by UPLC.

Synthesis Example 4

This example illustrates the preparation of a compound having Formula II, Compound H1-d.

The compound can be made using known C—C coupling techniques and deuteration techniques, according to the scheme shown below.

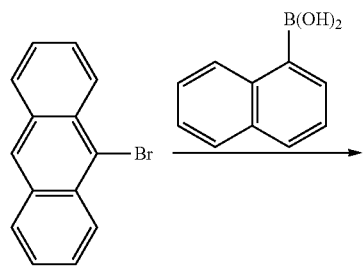

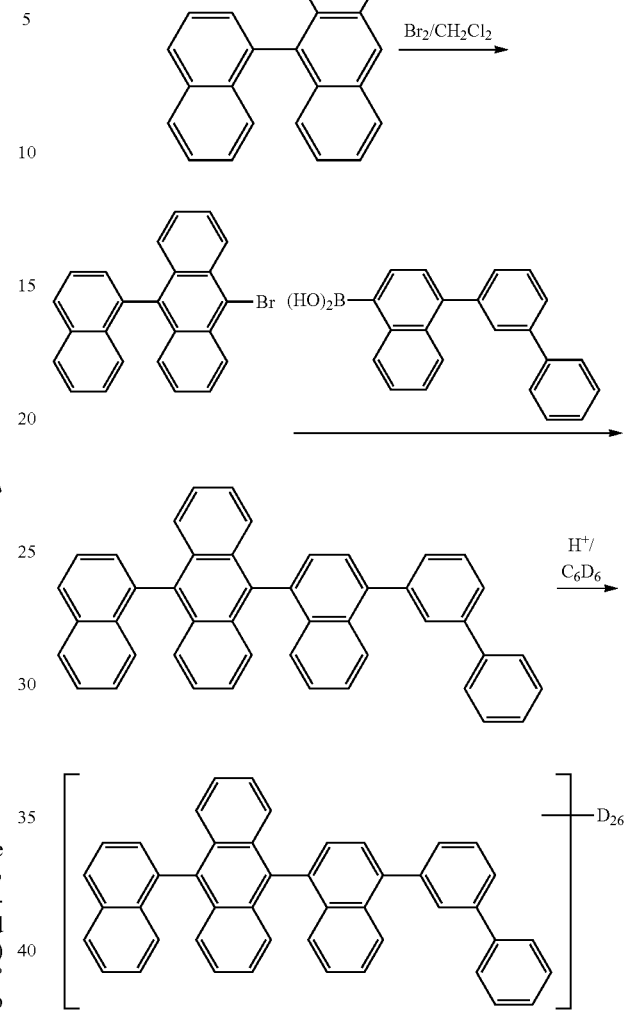

Synthesis Example 5

This example illustrates the preparation of a compound having Formula II, Compound H3.

The compound can be made using known C—C coupling techniques, according to the scheme shown below.

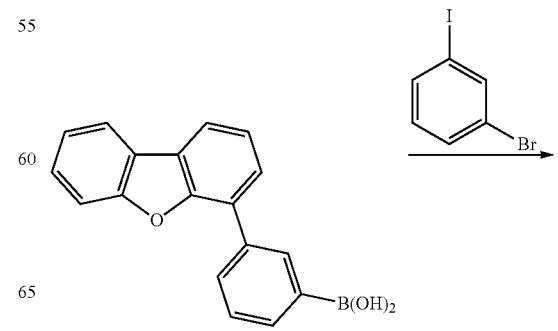

-continued

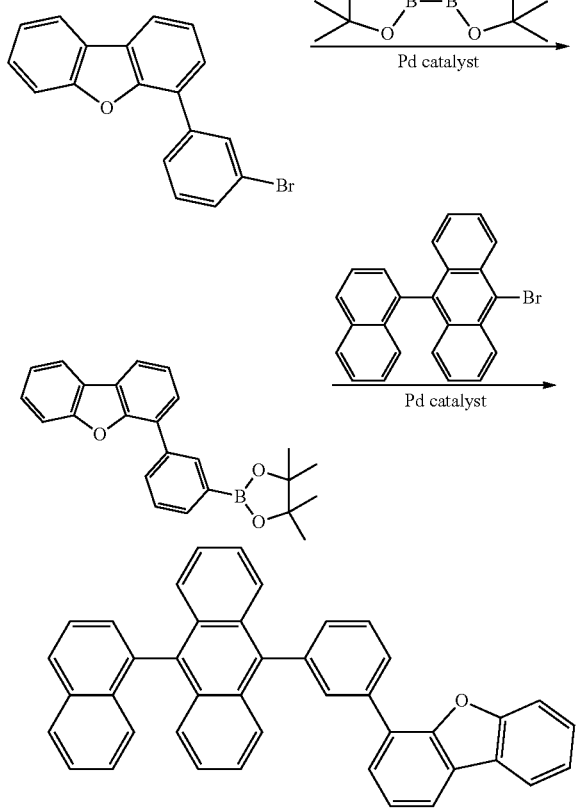

Device Examples (1) Materials

Comparative Host X is a deuterated naphthylanthracene that does not have the structure of Formula II. Host X has no phenyl group with a Q substituent in the meta position.

ET-1 is an aryl phosphine oxide.

ET-2 is lithium quinolate.

HIJ-1 is a hole injection material which is made from an aqueous dispersion of an electrically conductive polymer and a polymeric fluorinated sulfonic acid.

HIJ-2 is 1,4,5,8,9,12-hexaazatriphenylenehexacarbonitrile ("HAT-CN").

HTM-1 is a triarylamine polymer.

HTM-2 is a triarylamine polymer having binaphthyl groups.

HTM-3 is an triarylamine compound.

NPD is N,N'-di(1-naphthyl)-N,N'-diphenyl-(1,1'-biphenyl)-4,4'-diamine.

(2) Device Fabrication

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Device Type 1. Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent, to form a hole injection layer ("HIL"). After cooling, the substrates were then spin-coated with a solution of hole transport material and then heated to remove solvent, to form a hole transport layer ("HTL"). The workpieces were then placed in a vacuum chamber. The photoactive and host materials, electron transport materials, electron injection materials, and the Al cathode were then deposited sequentially by thermal evaporation using the appropriate masks, to form the photoactive layer or emissive layer ("EML"), the electron transport layer ("ETL"), and the electron injection layer ("EIL"), followed by the cathode. The chamber was vented, and the devices were encapsulated using a glass lid, desiccant, and UV curable epoxy.

Device Type 2: Immediately before device fabrication the cleaned, patterned ITO substrates were treated with UV ozone for 10 minutes. Immediately after cooling, an aqueous dispersion of HIJ-1 was spin-coated over the ITO surface and heated to remove solvent, to form a short reduction layer ("SRL"). The workpieces were then placed in a vacuum chamber. The hole injection material, one or more hole transport materials, the photoactive and host materials, electron transport materials, electron injection material, and the Al cathode were then deposited sequentially by thermal evaporation using the appropriate masks, to form the hole injection layer, one or more hole transport layers, the photoactive layer or emissive layer, the electron transport layer, and the electron injection layer, followed by the cathode. The chamber was vented, and the devices were encapsulated using a glass lid, desiccant, and UV curable epoxy.

(3) Device Characterization

The OLED devices were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W. The color coordinates were determined using either a Minolta CS-100 meter or a Photoresearch PR-705 meter.

Device Example 1 and Comparative Example A

This example illustrates the use of the photoactive composition described herein in a device. The device was made as described in Device Type 1.

In Example 1, the dopant was Compound D6, and the host was Compound H3.

In Comparative Example A, the dopant was Compound D6, and the host was Comparative Host X.

The devices had the following layers.

Anode=ITO (50 nm)
HIL=HIJ-1 (60 nm)
HTL=HTM-1 (19 nm)
EML=Host:Dopant in a 13:1 weight ratio (20 nm)
ETL=ET-1:ET-2 (3:2) (20 nm)
EIL=ET-2 (3.8 nm)
Cathode=Al (100 nm)

The results are given in Table 1 below.

TABLE 1

| Ex. | CE (cd/A) | EQE (%) | CIEX | CIEY | V at 15 mA/cm² | T95 (h) |
|---|---|---|---|---|---|---|
| Comp. A | 8.2 | 8.0 | 0.140 | 0.119 | 4.0 | 140 |
| 1 | 9.0 | 8.8 | 0.139 | 0.120 | 4.0 | 145 |

All data at 1000 nits, unless otherwise specified. CE is the current efficiency; EQE=external quantum efficiency; CIEX and CIEY refer to the x and y color coordinates according to the C.I.E. chromaticity scale (Commission Internationale de L'Eclairage, 1931); V is voltage; T95 is the time in hours to reach 95% of the initial luminance at 50° C. and a current density of 16.5 mA/cm².

Device Example 2 and Comparative Example B

This example illustrates the use of the photoactive composition described herein in a device. The device was made as described in Device Type 1.
In Example 2, the dopant was Compound D7, and the host was Compound H1-d.
In Comparative Example B, the dopant was Compound D7, and the host was Comparative Host X.
The devices had the following layers.
Anode=ITO (50 nm)
HIL=HIJ-1 (60 nm)
HTL=HTM-2 (19 nm)
EML=Host:Dopant in a 20:1 weight ratio (20 nm)
ETL=ET-1:ET-2 (3:2) (20 nm)
EIL=ET-2 (3.8 nm)
Cathode=Al (100 nm)
The results are given in Table 2 below.

TABLE 2

| Ex. | CE (cd/A) | EQE (%) | CIEX | CIEY | V at 15 mA/cm² | T95 (h) |
|---|---|---|---|---|---|---|
| Comp. B | 8.5 | 8.6 | 0.141 | 0.116 | 4.2 | 400 |
| 2 | 8.9 | 9.3 | 0.141 | 0.110 | 4.2 | 540 |

All data at 1000 nits, unless otherwise specified. CE is the current efficiency; EQE=external quantum efficiency; CIEX and CIEY refer to the x and y color coordinates according to the C.I.E. chromaticity scale (Commission Internationale de L'Eclairage, 1931); V is voltage; T95 is the time in hours to reach 95% of the initial luminance at 50° C. and a current density of 16.5 mA/cm².

Device Example 3 and Comparative Example C

This example illustrates the use of the photoactive composition described herein in a device. The device was made as described in Device Type 2, with two hole transport layers.
In Example 3, the dopant was Compound D8, and the host was Compound H1-d.
In Comparative Example C, the dopant was Compound D8, and the host was Comparative Host X.
The devices had the following layers.
Anode=ITO (50 nm)
SRL=HIJ-1 (100 nm)
HIL=HIJ-2 (7 nm)
HTL1=NPD (90 nm)
HTL2=HTM-3 (20 nm)
EML=Host:Dopant in a 32:1 weight ratio (25 nm)
ETL=ET-1:ET-2 (1:1) (26.2 nm)
EIL=ET-2 (3.5 nm)
Cathode=Al (100 nm)
The results are given in Table 3 below.

TABLE 3

| Ex. | CE (cd/A) | EQE (%) | CIEX | CIEY | V at 15 mA/cm² | T70 (h) |
|---|---|---|---|---|---|---|
| Comp. C | 8.3 | 9.2 | 0.141 | 0.100 | 6.3 | 155 |
| 3 | 8.6 | 10.8 | 0.143 | 0.084 | 6.3 | 240 |

All data at 1000 nits, unless otherwise specified. CE is the current efficiency; EQE=external quantum efficiency; CIEX and CIEY refer to the x and y color coordinates according to the C.I.E. chromaticity scale (Commission Internationale de L'Eclairage, 1931); V is voltage; T70 is the time in hours to reach 70% of the initial luminance at 50° C. and a current density of 16.5 mA/cm².

Device Example 4 and Comparative Example D

This example illustrates the use of the photoactive composition described herein in a device. The device was made as described in Device Type 2, except that there was no SRL.
In Example 4, the dopant was Compound D6, and the host was Compound H1-d.
In Comparative Example D, the dopant was Compound D6, and the host was Comparative Host X.
The devices had the following layers.
Anode=ITO (50 nm)
HIL=HIJ-2 (10 nm)
HTL1=NPD (168 nm)
HTL2=HTM-3 (20 nm)
EML=Host:Dopant in a 20:1 weight ratio (25 nm)
ETL=ET-1:ET-2 (1:1) (24.2 nm)
EIL=ET-2 (3.5 nm)
Cathode=Al (100 nm)
The results are given in Table 4 below.

TABLE 4

| Ex. | CE (cd/A) | EQE (%) | CIEX | CIEY | V at 15 mA/cm2 | T95 (h) |
|---|---|---|---|---|---|---|
| Comp. D | 9.2 | 8.9 | 0.144 | 0.120 | 5.7 | 260 |
| 4 | 9.2 | 9.2 | 0.144 | 0.114 | 5.8 | 250 |

All data at 1000 nits, unless otherwise specified. CE is the current efficiency; EQE=external quantum efficiency; CIEX and CIEY refer to the x and y color coordinates according to the C.I.E. chromaticity scale (Commission Internationale de L'Eclairage, 1931); V is voltage; T95 is the time in hours to reach 95% of the initial luminance at 50° C. and a current density of 16.5 mA/cm².

Device Example 5 and Comparative Example E

This example illustrates the use of the photoactive composition described herein in a device. The device was made as described in Device Type 2, except that there was no SRL.

In Example 5, the dopant was Compound D9, and the host was Compound H1-d.

In Comparative Example E, the dopant was Compound D9, and the host was Comparative Host X.

The devices had the following layers.
Anode=ITO (50 nm)
HIL=HIJ-2 (10 nm)
HTL1=NPD (168 nm)
HTL2=HTM-3 (20 nm)
EML=Host:Dopant in a 20:1 weight ratio (25 nm)
ETL=ET-1:ET-2 (1:1) (24.2 nm)
EIL=ET-2 (3.5 nm)
Cathode=Al (100 nm)

The results are given in Table 5 below.

TABLE 5

Device results

| Ex. | CE (cd/A) | EQE (%) | CIEX | CIEY | V at 15 mA/cm2 | T80 (h) |
|---|---|---|---|---|---|---|
| Comp. E | 8.2 | 7.8 | 0.141 | 0.124 | 5.7 | 658 |
| 5 | 8.5 | 8.3 | 0.141 | 0.118 | 5.9 | 570 |

All data at 1000 nits, unless otherwise specified. CE is the current efficiency; EQE=external quantum efficiency; CIEX and CIEY refer to the x and y color coordinates according to the C.I.E. chromaticity scale (Commission Internationale de L'Eclairage, 1931); V is voltage; T80 is the time in hours to reach 80% of the initial luminance at 50° C. and a current density of 16.5 mA/cm$^2$.

It can be seen from the above results that devices made with the photoactive composition described herein have higher efficiency and/or better color (lower C.I.E. y-coordinate) and/or longer lifetime.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

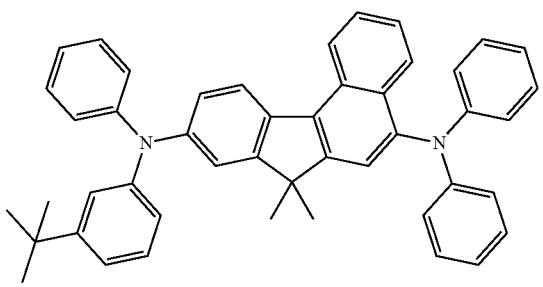

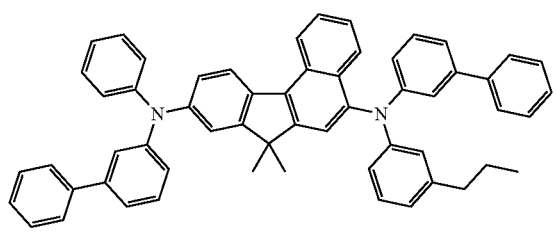

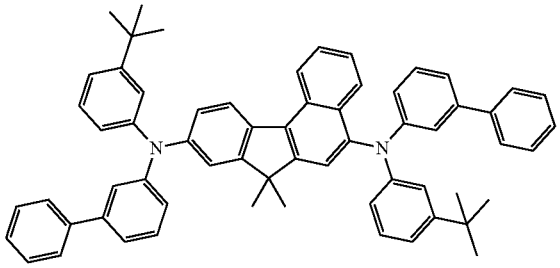

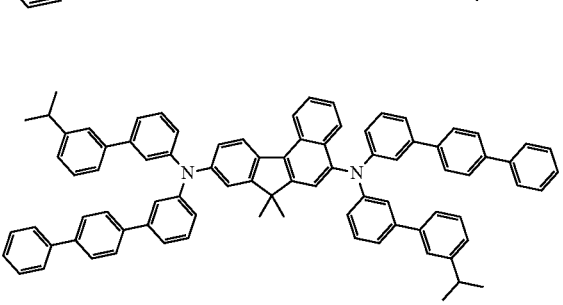

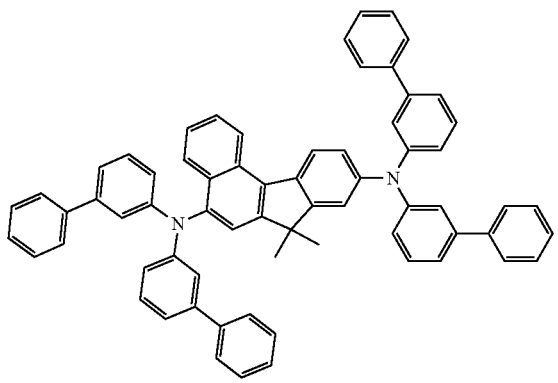

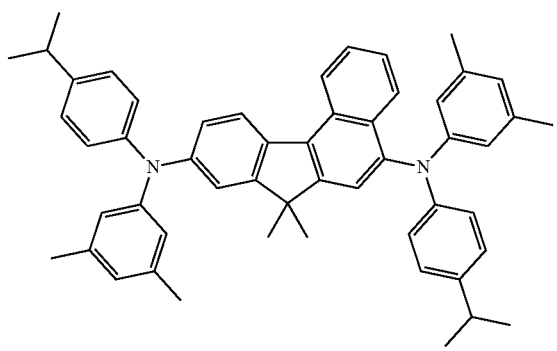

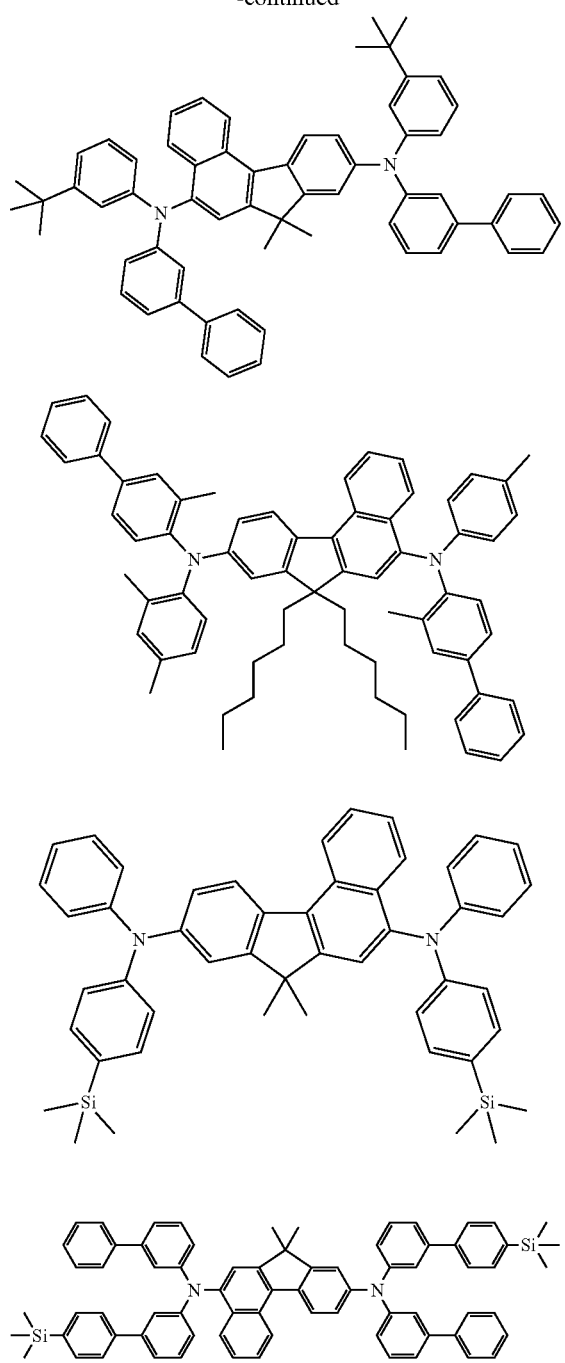
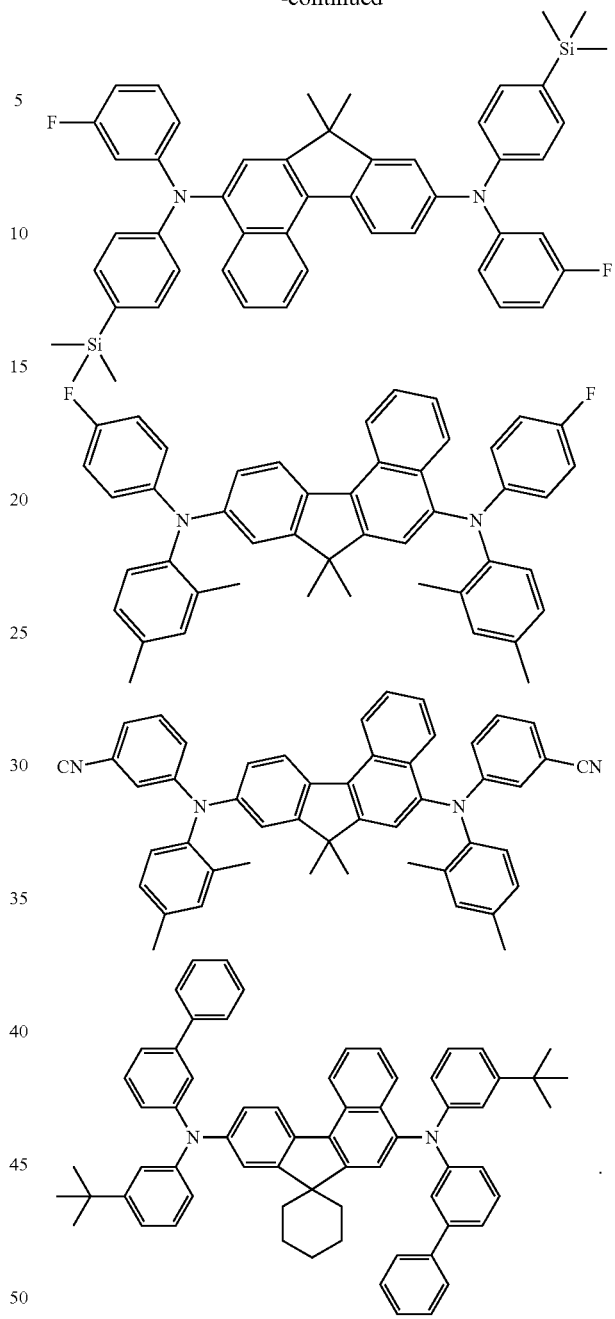

What is claimed is:
1. A photoactive composition comprising:
(a) a dopant material having Formula I

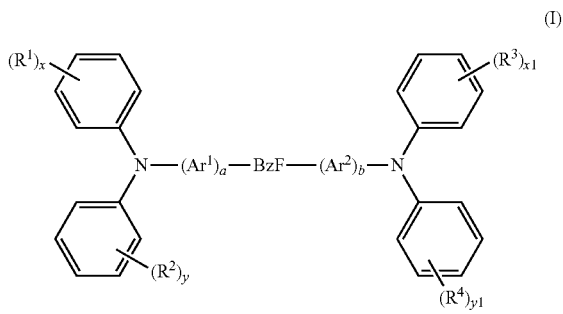

wherein:
Ar$^1$ and Ar$^2$ are the same or different and are selected from the group consisting of hydrocarbon aryl and deuterated hydrocarbon aryl;
R$^1$-R$^4$ are the same or different at each occurrence and are selected from the group consisting of D, F, CN, alkyl, fluoroalkyl, aromatic hydrocarbon having one point of attachment, fluorinated aromatic hydrocarbon having one point of attachment, N-heteroaromatic hydrocarbon having one point of attachment, amino, silyl, germyl, alkoxy, RO— where R is an aromatic hydrocarbon having one point of attachment, fluoroalkoxy, siloxane, siloxy, deuterated alkyl, deuterated partially-fluorinated alkyl, deuterated aromatic hydrocarbon having one point of attachment, deuterated partially-fluorinated aromatic hydrocarbon having one point of attachment, deuterated N-heteroaromatic hydrocarbon having one point of attachment, deuterated amino, deuterated silyl, deuterated germyl, deuterated alkoxy, deuterated RO— where R is an aromatic hydrocarbon having one point of attachment, deuterated fluoroalkoxy, deuterated siloxane, and deuterated siloxy;
a and b are the same or different and are 0 or 1;
x, x1, y, and y1 are the same or different and are an integer from 0-5; and
BzF has formula BzF-1

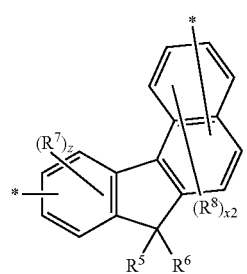

where
R$^5$ and R$^6$ are the same or different at each occurrence and are selected from the group consisting of alkyl, fluoroalkyl, aromatic hydrocarbon having one point of attachment, fluorinated aromatic hydrocarbon having one point of attachment, deuterated alkyl, deuterated fluoroalkyl, deuterated aromatic hydrocarbon having one point of attachment, and deuterated fluorinated aromatic hydrocarbon having one point of attachment, where two $R^5$ and $R^6$ alkyl groups can be joined together to make a cycloalkyl ring, and where two $R^5$ and $R^6$ phenyl groups can be joined to form a fluorene group;

$R^7$ and $R^8$ are the same or different at each occurrence and are selected from the group consisting of D, F, CN, alkyl, fluoroalkyl, aromatic hydrocarbon having one point of attachment, fluorinated aromatic hydrocarbon having one point of attachment, N-heteroaromatic hydrocarbon having one point of attachment, amino, silyl, germyl, alkoxy, RO— where R is an aromatic hydrocarbon having one point of attachment, fluoroalkoxy, siloxane, siloxy, deuterated alkyl, deuterated partially-fluorinated alkyl, deuterated aromatic hydrocarbon having one point of attachment, deuterated partially-fluorinated aromatic hydrocarbon having one point of attachment, deuterated N-heteroaromatic hydrocarbon having one point of attachment, deuterated amino, deuterated silyl, deuterated germyl, deuterated alkoxy, deuterated RO— where R is an aromatic hydrocarbon having one point of attachment, deuterated fluoroalkoxy, deuterated siloxane, and deuterated siloxy;

x2 is an integer from 0-5;

z is an integer from 0-3; and indicates a point of attachment; and (b) a host material having Formula II

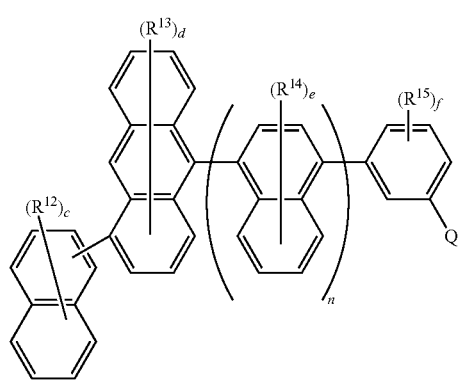

wherein:

Q is selected from the group consisting of aromatic hydrocarbon having one point of attachment, aromatic hydrocarbon having at least one heteroatom in the ring structure and one point of attachment, deuterated aromatic hydrocarbon having one point of attachment, and deuterated aromatic hydrocarbon having at least one heteroatom in the ring structure and one point of attachment;

$R^{12}$-$R^{15}$ are the same or different at each occurrence and are selected from the group consisting of D, F, CN, alkyl, fluoroalkyl, aromatic hydrocarbon having one point of attachment, fluorinated aromatic hydrocarbon having one point of attachment, aromatic hydrocarbon having at least one heteroatom in the ring structure and one point of attachment, silyl, germyl, alkoxy, RO— where R is an aromatic hydrocarbon having one point of attachment, fluoroalkoxy, siloxane, siloxy, deuterated alkyl, deuterated partially-fluorinated alkyl, deuterated hydrooarbon aryl aromatic hydrocarbon having one point of attachment, deuterated partially-fluorinated af14 aromatic hydrocarbon having one point of attachment, deuterated heteroaryl aromatic hydrocarbon having at least one heteroatom in the ring structure and one point of attachment, deuterated silyl, deuterated germyl, deuterated alkoxy, deuterated aryloxy RO— where R is an aromatic hydrocarbon having one point of attachment, deuterated fluoroalkoxy, deuterated siloxane, and deuterated siloxy;

c is an integer from 0-7;

d is an integer from 0-8;

e is an integer from 0-6;

f is an integer from 0-4; and n is 1.

2. The composition of claim 1, wherein the dopant has Formula I-a

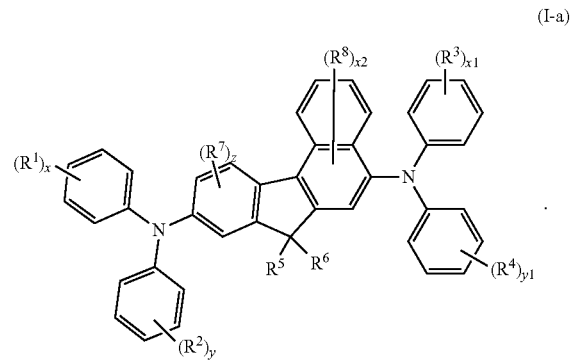

3. The composition of claim 1, wherein the dopant has Formula I-b

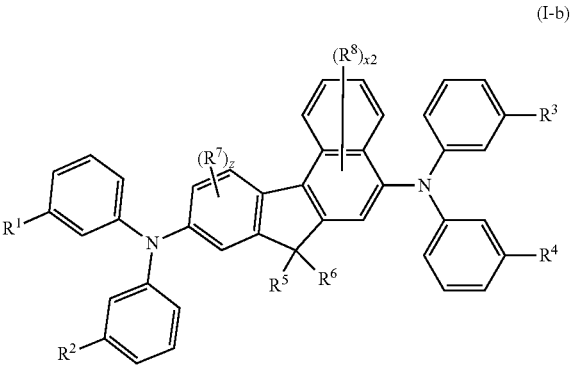

with the proviso that at least one of $R^1$-$R^4$ is not D.

4. The composition of claim 1, wherein $R^1$-$R^4$ have no heteroaromatic groups.

5. The composition of claim 1, wherein x>0 and at least one $R^1$ is an N-heteroaryl having one point of attachment or deuterated N-heteroaryl having one point of attachment.

6. The composition of claim 5, wherein the N-heteroaryl having one point of attachment is a carbazole or the deuterated N-heteroaryl having one point of attachment is a deuterated carbazole.

7. The composition of claim 1, wherein x>0 and at least one $R^1$ is an alkyl or deuterated alkyl having 1-20 carbons.

8. The composition of claim 1, wherein x>0 and at least one $R^1$ is a hydrocarbon aryl group having 6-36 ring carbons, the hydrocarbon aryl group having one point of attachment.

9. The composition of claim 1, wherein x>0 and at least one $R^1$ is selected from the group consisting of phenyl, naphthyl, deuterated phenyl, deuterated naphthyl, and Formula a

[Formula a]

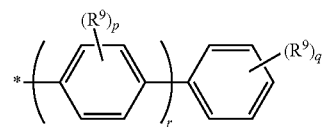

where:
  $R^9$ is the same or different at each occurrence and is selected from the group consisting of D, F, CN, alkyl, fluoroalkyl, hydrocarbon aryl, fluoroaryl, N-heteroaryl, amino, silyl, germyl, alkoxy, aryloxy, fluoroalkoxy, siloxane, siloxy, deuterated alkyl, deuterated partially-fluorinated alkyl, deuterated hydrocarbon aryl, deuterated partially-fluorinated aryl, deuterated N-heteroaryl, deuterated amino, deuterated silyl, deuterated germyl, deuterated alkoxy, deuterated aryloxy, deuterated fluoroalkoxy, deuterated siloxane, and deuterated siloxy, where adjacent R9 groups can be joined together to form an fused aromatic ring or a deuterated fused aromatic ring;
  p is the same or different at each occurrence and is an integer from 0-4;
  q is an integer from 0-5;
  r is an integer from 1 to 5; and
  indicates the point of attachment.

10. The composition of claim 9, wherein x>0 and at least one $R^1$ has one or more substituents selected from the group consisting of D, F, CN, alkyl, silyl, germyl, hydrocarbon aryl, deuterated alkyl, deuterated silyl, deuterated germyl, and deuterated hydrocarbon aryl.

11. The composition of claim 1, wherein Q is a hydrocarbon aryl group or deuterated aryl group having 6-36 ring carbons and has no heteroaromatic groups.

12. The composition of claim 1, wherein Q is a heteroaryl having at least one ring atom which is selected from the group consisting of N, O, and S.

13. The composition of claim 1, wherein the host compound having Formula II is at least 10% deuterated.

14. The composition of claim 1, wherein at least one of x, y, x1, or y1 is non-zero.

15. The composition of claim 1, wherein the dopant material is one of the following compounds: